US008716191B2

(12) United States Patent
Winssinger et al.

(10) Patent No.: US 8,716,191 B2
(45) Date of Patent: May 6, 2014

(54) METHOD OF PREPARING AN ADDUCT

(75) Inventors: Nicolas Winssinger, Strasbourg (FR); Sofia Barluenga, Strasbourg (FR)

(73) Assignees: Universite de Strasbourg, Strasbourg (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/378,675

(22) PCT Filed: Jun. 22, 2010

(86) PCT No.: PCT/IB2010/001932
§ 371 (c)(1),
(2), (4) Date: Jan. 30, 2012

(87) PCT Pub. No.: WO2010/150103
PCT Pub. Date: Dec. 29, 2010

(65) Prior Publication Data
US 2012/0115751 A1 May 10, 2012

Related U.S. Application Data

(60) Provisional application No. 61/219,186, filed on Jun. 22, 2009.

(51) Int. Cl.
*C40B 30/04* (2006.01)
*C40B 40/06* (2006.01)
*C12Q 1/68* (2006.01)
*G01N 33/53* (2006.01)

(52) U.S. Cl.
USPC .................... 506/9; 506/16; 435/6.1; 435/7.1

(58) Field of Classification Search
USPC ............................................................ 506/9
See application file for complete search history.

(56) References Cited

U.S. PATENT DOCUMENTS

2012/0021940 A1* 1/2012 Guthold et al. .................. 506/9

FOREIGN PATENT DOCUMENTS

| WO | 0023458 A1 | 4/2000 |
| WO | 02/099078 A2 | 12/2002 |
| WO | 03/076943 A1 | 9/2003 |
| WO | 2005/058479 A2 | 6/2005 |
| WO | 2006/053571 A2 | 5/2006 |
| WO | 2007/053358 A2 | 5/2007 |

OTHER PUBLICATIONS

Wrenn et al., "Synthetic Ligands Discovered by in Vitro Selection," J. Am. Chem. Soc. 2007, 129:13137-13143.*
Perry, "Solid-Phase Sequencing of Biotinylated PCR Products with Streptavidin-Coated Magnetic Beads," Methods Mol. Med. 1999, 31:49-54.*
Pianowski Zbigniew L et al: "Nucleic acid encoding to program self-assembly in chemical biology", Chemical Society Reviews Jul. 2008, vol. 37, No. 7, Jul. 2008, pp. 1330-1336, XP8131490.

(Continued)

*Primary Examiner* — Samuel Woolwine
*Assistant Examiner* — Kaijiang Zhang
(74) *Attorney, Agent, or Firm* — Young & Thompson

(57) ABSTRACT

A method for identifying one or several molecular structure (s) having a high-affinity for a target of interest, the molecular structure(s) each including one nucleotide chain onto which is hybridized at least one PNA-encoded molecule.

2 Claims, 19 Drawing Sheets

(56) References Cited

OTHER PUBLICATIONS

Debaene F et al: "Expanding the scope of PNA-encoded libraries: divergent synthesis of libraries targeting cysteine, serine and metalloproteases as well as tyrosine phosphatases", Tetrahedron, Elsevier Science Publishers, Amsterdam, NL, vol. 63, No. 28, Jul. 9, 2007, pp. 6577-6586, XP025320925.
Harris Jennifer L et al: "PNA encoding (PNA=peptide nucleic acid): from solution-based libraries to organized microarrays", Chem. Eur. J., vol. 11, No. 23, Nov. 18, 2005, pp. 6792-6801, XP002616635.
Gartner Z J et al: "DNA-templated organic synthesis and selection of a library of macrocycles", Science, American Association for the Advancement of Science, US, vol. 305, No. 5690, Sep. 10, 2004, pp. 1601-1605, XP002397753.
Halpin David R et al: "DNA display II. Genetic manipulation of combinatorial chemistry libraries for small-molecule VV- evolution", PLOS Biology, Public Library of Science, US, vol. 2, No. 7, Jul. 1, 2004, pp. 1022-1030, XP002424416.
Halpin David R et al: "DNA display III. Solid-phase organic synthesis on unprotected DNA", PLOS Biology, vol. 2, No. 7, Jul. 2004, pp. 1031-1038, XP002616636.
International Search Report, dated Jan. 13, 2011, in PCT/IB2010/001932.

\* cited by examiner

| | | |
|---|---|---|
| 1 |  | no significant binding |
| 2 |  | no significant binding |
| 3 |  | no significant binding |
| 4 |  | no significant binding |
| 5 |  | no significant binding |
| 6 |  | no significant binding |
| 7 |  | no significant binding |
| 8 |  | no significant binding |
| 9 |  | no significant binding<br>no significant binding |

| 10 |  no significant binding |
|---|---|
| 11 |  no significant binding |
| 12 |  $k_a = 319, k_d = 0.00135, K_D = 4.24\ \text{nM}$ |
| 13 |  $k_a = 197, k_d = 0.00160, K_D = 8.12\ \text{nM}$ |
| 14 |  $k_a = 183, k_d = 0.00317, K_D = 17.3\ \text{nM}$ |
| 15 |  $k_a = 97, k_d = 0.0087, K_D = 89.4\ \text{nM}$ |
| 16 |  $k_a = 507, k_d = 0.00324, K_D = 6.39\ \text{nM}^*$ |
| 17 |  $k_a = 151, k_d = 0.00179, K_D = 11.9\ \text{nM}$ |

METHOD OF PREPARING AN ADDUCT

The present invention relates to methods for identifying one or several consensus structure(s) having a high-affinity for a chemical target of interest, and to a method of preparing an adduct starting from said potential consensus structure(s).

The discovery of selective ligands to a protein remains a rate limiting step in drug discovery. While classical high throughput screening has proven successful for the screening of libraries of tens of thousands to hundreds of thousands of compounds, it is prohibitively expensive and cumbersome to scale out this technology on a proteomic scale. The approach proposed herein aims to overcome these limitations in providing a technology which enables the selection and evolution of small molecules from readily available libraries containing up to millions of compounds obtained by self assembly of PNA-encoded libraries onto DNA-templates in a highly miniaturized format. The inventors have developed technologies to synthesize PNA-encoded small molecule libraries by mix and split combinatorial synthesis (Harris, J. L. & Winssinger, N. (2005) PNA encoding (PNA=peptide nucleic acid): From solution-based libraries to organized microarrays Chem. Eur. J. 11: 6792-6801) and demonstrated several approaches to select the fittest ligand and decode its identity by hybridization to an oligonucleotide array (Pianowski, Z. L. & Winssinger, N. (2008) Nucleic acid encoding to program self-assembly in chemical biology Chem. Soc. Rev. 37: 1330-6; Debaene, F., Da Silva, J., Pianowski, Z., Duran, F. & Winssinger, N. (2007) Expanding the scope of PNA-encoded libraries: divergent synthesis of libraries targeting cysteine, serine and metalloproteases as well as tyrosine phosphatases Tetrahedron 63: 6577-6586; Urbina, H. D., Debaene, F., Jost, B., Bole-Feysot, C., Mason, D. E., Kuzmic, P., Harris, J. L. & Winssinger, N. (2006) Self-assembled small-molecule microarrays for protease screening and profiling ChemBioChem 7: 1790-1797; Harris, J., Mason, D. E., Li, J., Burdick, K. W., Backes, B. J., Chen, T., Shipway, A., Van Heeke, G., Gough, L., Ghaemmaghami, A., Shakib, F., Debaene, F. & Winssinger, N. (2004) Activity Profile of Dust Mite Allergen Extract Using Substrate Libraries and Functional Proteomic Microarrays Chemistry & Biology 11: 1361-1372).

Peptide nucleic acids (Nielsen, P. E. (2004) PNA technology Mol. Biotech. 26: 233-248; Egholm, M., Buchardt, O., Christensen, L., Behrens, C., Freier, S. M., Driver, D. A., Berg, R. H., Kim, S. K., Norden, B. & Nielsen, P. E. (1993) PNA hybridizes to complementary oligonucleotides obeying the Watson-Crick hydrogen-bonding rules Nature 365: 566-8) are attractive tags to program self assemblies as its chemistry is significantly more permissive than natural oligonucleotides and its higher affinity for natural oligonucleotides allow for shorter tags which are more specific and less sensitive to the ionic strength of the solution. The synthesis of such libraries is at present fully automated and libraries of thousands of compounds can be readily prepared.

There are several technologies to quantify large collection of DNA fragments including DNA microarrays (custom arrays are available from Agilent with over 200 000 discrete sequence of 60 nucleotides) or high throughput sequencing technologies such as SOLiD (ABI) or Solexa (Illumina) sequencers which have a sequence coverage of over 10 000 000 sequences of 40 or more nucleotide in a single sequencing run. DNA-encoded libraries have been reported by academic groups and companies (Ensemble Discovery Corporation (http://www.ensemblediscovery.com/), Nuevolution (http://www.nuevolution.com/), Vipergen ApS (http://www.vipergen.com/), Philochem AG (http://www-.philochem.ch/), and Praecis Pharmaceuticals (see for example WO 2007/011722, WO2006/138560, WO 02/074929 and WO 03/076943). Ensemble Discovery is based on the DNA-templated synthesis technology developed by D. Liu at Harvard (Tse, B. N., Snyder, T. M., Shen, Y. & Liu, D. R. (2008) Translation of DNA into a library of 13,000 synthetic small-molecule macrocycles suitable for in vitro selection J. Am. Chem. Soc. 130: 15611-26; Li, X. & Liu, D. R. (2004) DNA-templated organic synthesis: Nature's strategy for controlling chemical reactivity applied to synthetic molecules Angew. Chem., Int. Ed. 43: 4848-4870; Gartner, Z. J., Tse, B. N., Grubina, R., Doyon, J. B., Snyder, T. M. & Liu, D. R. (2004) DNA-templated organic synthesis and selection of a library of macrocycles Science 305: 1601-5) and programs the selective delivery of reagents to diversify a small molecule appended at the 5'-end of the encoding strand (FIG. 2). Viprogen utilizes a similar approach but using a more complex hybridization architecture to confine the reagent within a cavity formed by the nucleic acids (Hansen, M. H., Blakskjaer, P., Petersen, L. K., Hansen, T. H., Hoejfeldt, J. W., Gothelf, K. V. & Hansen, N. J. V. (2009) A Yoctoliter-Scale DNA Reactor for Small-Molecule Evolution J. Am. Chem. Soc. 131: 1322-1327). Praecis (Clark, M. A., Acharya, R. A., Arico-Muendel, C. C., Belyanskaya, S. L., Benjamin, D. R., Carlson, N. R., Centrella, P. A., Chiu, C. H., Creaser, S. P., Cuozzo, J. W., Davie, C. P., Ding, Y., Franklin, G. J., Franzen, K. D., Gefter, M. L., Hale, S. P., Hansen, N. J., Israel, D. I., Jiang, J., Kavarana, M. J., Kelley, M. S., Kollmann, C. S., Li, F., Lind, K., Mataruse, S., Medeiros, P. F., Messer, J. A., Myers, P., O'Keefe, H., Oliff, M. C., Rise, C. E., Satz, A. L., Skinner, S. R., Svendsen, J. L., Tang, L., van Vloten, K., Wagner, R. W., Yao, G., Zhao, B. & Morgan, B. A. (2009) Design, synthesis and selection of DNA-encoded small-molecule libraries Nat. Chem. Biol. 5: 647-54) and Phylochem (Melkko, S., Mannocci, L., Dumelin, C. E., VIIIa, A., Sommavilla, R., Zhang, Y., Gruetter, M. G., Keller, N., Jermutus, L., Jackson, R. H., Scheuermann, J. & Neri, D. (2010) Isolation of a Small-Molecule Inhibitor of the Antiapoptotic Protein Bcl-xL from a DNA-Encoded Chemical Library ChemMedChem 5: 584-590; Buller, F., Zhang, Y., Scheuermann, J., Schafer, J., Buhlmann, P. & Neri, D. (2009) Discovery of TNF Inhibitors from a DNA-Encoded Chemical Library based on Diels-Alder Cycloaddition Chem. Biol. 16: 1075-1086; Melkko, S., Scheuermann, J., Dumelin, C. E. & Neri, D. (2004) Encoded self-assembling chemical libraries Nat. Biotechnol. 22: 568-574) use a split and mix combinatorial synthesis whereby every reaction of diversification is followed by a enzymatic mediated extension of the encoding strand.

In addition, D. Harbury at Stanford University (Wrenn, S. J., Weisinger, R. M., Halpin, D. R. & Harbury, P. B. (2007) Synthetic Ligands Discovered by in Vitro Selection J. Am. Chem. Soc. 129: 13137-13143; Halpin, D. R., Lee, J. A., Wrenn, S. J. & Harbury, P. B. (2004) DNA display. III. Solid-phase organic synthesis on unprotected DNA PLoS Biol. 2: 1031-1038) has developed a technology based on routing nucleic acids through different diversification pathways by hybridizing the mixture to resins containing complementary strands. In all cases, the diversification and encoding reactions must be performed in water under conditions which do not degrade the DNA which in itself is a severe limitation on the repertoire of reactions that can be utilized to construct the libraries. Further limitations for technologies which rely on an enzymatic transformation to extend the nucleic acid tag (Praecis and Phylochem) is the possibility of enzyme poisoning with small molecules present in the library or reagents left from the previous transformations.

Finally, perhaps the most important consideration is the selection of the fittest ligand from very large libraries. All the technologies use the same approach which has been successfully used for phage display and aptamers (Selex): the target is immobilized and the library is panned, washing the target to remove non specific interactions and ultimately, recover the best binder with a more stringent wash. Since the total library concentration cannot exceed a given concentration without engendering artifacts on the target protein (most likely in the µM range), as the library size increase, the concentration of individual compounds decrease. For a library of one million compounds, a total library concentration of 10 µM results in a 10 pM concentration for each library member. While it is unlikely that a small molecule can have a 10 pM affinity for a target protein, as long as the protein concentration is above the Kd of the interaction (for example >100 nM), binders with lower Kd will be captured by the protein. It is thus very important to be able to amplify the product of a selected nucleic-acid encoded small molecule screen to reiterate the selection process. This has been demonstrated for the technology developed in a pilot library by D. Liu (Gartner, Z. J., Tse, B. N., Grubina, R., Doyon, J. B., Snyder, T. M. & Liu, D. R. (2004) DNA-templated organic synthesis and selection of a library of macrocycles Science 305: 1601-5) and D. Harbury (Wrenn, S. J., Weisinger, R. M., Halpin, D. R. & Harbury, P. B. (2007) Synthetic Ligands Discovered by in Vitro Selection J. Am. Chem. Soc. 129: 13137-13143) but is not possible with libraries made by Praecis and Phylochem. It should be noted however that the practicality and speed for such amplification will ultimately be an important criterion.

There is consequently a need for a more rapid, easy and economic technology for the selection of fittest ligands for a specific target.

The inventors have discovered a way to capitalize on the programmable assembly of these PNA-tagged small molecules onto libraries of DNA templates to be able to amplify the nucleic acid tag by PCR. This technique allows a very sensitive detection of the selected entity by virtue of the exponential amplification of the PCR reaction. An additional advantage of displaying PNA-encoded small molecules onto DNA templates is that it allows to combinatorially display small molecules as fragments of a ligand.

One purpose of the invention is thus to provide a method for identifying one or several molecular structure(s) having a high-affinity for a target of interest, each molecular structure(s) comprising one nucleotide chain onto which is hybridized at least one PNA-encoded molecule and said method comprising the following steps:
a) providing at least one library of PNA-encoded molecules and a library of nucleotide chains,
b) hybridizing said at least one library of PNA-encoded molecules onto said library of nucleotide chains,
c) bringing into contact the resulting library of PNA-encoded molecule(s)/nucleotide chain hybrid(s) lastly obtained with said target of interest,
d) selecting the fittest PNA-encoded molecule(s)/nucleotide chain hybrid(s) for the target of interest,
e) amplifying nucleotide chain(s) obtained from the previously mentioned fittest PNA-encoded molecule(s)/nucleotide chain hybrid(s),
f) optionally bringing into contact said nucleotide chain(s) previously amplified with one or more library of PNA-encoded molecules, the latter respectively having a content identical to that of said library or libraries of PNA-encoded molecules selected in step a), or containing some modification, then hybridizing them and repeating steps c) to e),
g) identifying said nucleotide chain(s) obtained in step e) or f), each corresponding to at least one PNA-encoded molecule of the at least one library of PNA-encoded molecules mentioned in step a).

In case where only one library of PNA-encoded molecules is hybridized onto said library of nucleotide chains i.e. in case where no more than one PNA-encoded molecule is hybridized onto each chain of said library of nucleotide chain(s), the resulting library of PNA-encoded molecule(s)/nucleotide chain hybrid(s) cannot be a combinatorial library. However, if two or more libraries of PNA-encoded molecules are hybridized onto said library of nucleotide chains i.e. in case where two or more PNA-encoded molecule(s) are hybridized onto at least one chain of said library of nucleotide chain(s), the resulting library of PNA-encoded molecule(s)/nucleotide chain hybrid(s) is combinatorial.

By the expression "molecular structure" is meant a display of one or more identifiable molecule(s) to a target of interest, wherein said one or more identifiable molecule(s) binds or concomitantly bind (respectively) in a specific manner to a target of interest and wherein said one or more identifiable molecule(s) is or are individually appended to a PNA chain hybridized onto a nucleotide chain.

By the expression "PNA-encoded molecule" is thus meant a small molecule which is PNA-tagged. According to the invention, preferred synthetic or natural molecules to be PNA-tagged are chosen among, but not limited to, amino acids, peptides, peptoids, antibodies, heterocycles selected from the groups comprising compounds having therapeutical efficacy and which are very well known from the person skilled in the art, such as benzodiazepines, secondary metabolites such as salicylic acid or erythromycin, carbohydrates and glycan mimetics. PNA-encoded molecules libraries may be obtained by chemical synthesis, in particular combinatorial chemistry, co-synthesis or chemical coupling reactions or are commercially available. The PNA chain of the PNA-encoded molecule is constituted of 6 to 30-mer PNA, preferably 10 to 20-mer PNA.

By the expression "high-affinity for a target" is meant that the affinity is sufficient to be useful in a diagnostic or therapeutic application and typically is micromolar or below.

By the expression "target of interest" is meant any compound including, but not limited to, proteins such as protein complexes, receptors, enzymes, such as kinases and proteases, antibodies and antigens.

By the expression "nucleotide chains" is meant DNA, RNA or a mixture thereof.

By the expression "PNA(s)-nucleotide chain hybrid" is meant a compound which consists of a nucleotide chain onto which at least one, but preferably two PNA-encoded molecule(s) or multiple PNA-encoded molecules are hybridized. According to the invention, the resulting library of PNA(s)-nucleotide chain hybrids self assembles into predictable hybrids based on the rules of hybridization and nucleotide recognition. The identity of the molecules(s) can be inferred by the sequence of the nucleotide chain. Hybridization of multiple PNA-encoded molecules onto a nucleotide chain enables a combinatorial display of the PNA-encoded molecules which can interact cooperatively with a target of interest.

According to the invention, the library of PNA-encoded molecules may be obtained by any techniques known from the one skilled in the art, for examples by those disclosed by Winssinger et al. 2006, 2007 and 2008 cited above or described herein in examples. The person having ordinary skill in the art is able to choose libraries for which there is a fighting chance of obtaining molecular structure(s) having a high-affinity for said chosen target of interest. However, the skilled person may also choose, on a trial basis, libraries containing up to millions of PNA-encoded molecules which he pre-selected without certainty of obtaining molecular structure(s) having a high affinity for said target of interest.

According to the invention, the target of interest may be free in the reaction medium or may be fixed on any support known in the art, for example magnetic beads or surface-plasam resonance sensors chip. To select the fittest PNA-encoded molecule(s)/nucleotide chain hybrid(s) having the highest affinity for a target of interest the skilled person may use any known technique, for example a wash of the immobilized target to remove non specific interactions and ultimately recover said fittest combination(s) with more stringent conditions.

According to the invention, to amplify the nucleotide chain(s) obtained from the selection of the fittest combination, the skilled person may use any known technique, for example a PCR. Amplification in fungi or bacteria may also be suitable.

By the expression "containing some modification" is meant that the libraries of PNA-molecules may contain some changes at each round of selection in analogy to natural evolution where amplification is associated with some diversification.

By the expression "each corresponding to at least one PNA-encoded molecule" is meant that the identification of each known nucleotide chain may allow to find which PNA-encoded molecule(s) where hybridized onto said nucleotide chain and then to deduce which particular display(s) of said PNA-tagged molecule(s) were binding to said target of interest.

In a preferred embodiment, the method previously described is a method wherein the step f) is repeated until a convergence towards one or several consensus sequence(s) is obtained, preferably less than 20 times, still more preferably less than 5 times. In some cases, a consensus sequence may be obtained with only 1 to 3 repetitions.

According to the invention, the PNA chain can have any length, but advantageously comprises between 6 and 30-mer, preferably between 10 to 20-mer.

In another preferred embodiment, the method according to any previous definition is a method wherein said nucleotide chains only consist of DNA.

The present invention also has for object a method for identifying one or several consensus structure(s) having a high affinity for a target of interest comprising a method according to any previous definition, further comprising the following step:

h) determining at least one consensus structure starting from the nucleotide chain(s) identified in step g), said at least one consensus structure having a high-affinity to said target of interest.

By the expression "consensus structure(s)" is meant a set of one or several PNA-encoded molecule(s)/nucleotide chain hybrid(s) which have been repeatedly obtained in screening assays which allow selection of fittest PNA-encoded molecule(s)/nucleotide chain hybrid(s) for the target of interest. The consensus structure(s) may include said experimentally obtained PNA-encoded molecule(s)/nucleotide chain hybrid(s) differing from each other by the displayed molecule(s) (including wholly different molecules and molecules differing only by a few groups), the distance between said displayed molecule(s) and/or the order in which said molecule(s) is or are displayed (respectively), provided that this or these variation(s) does or do not involve a substantial change in the affinity of the displayed molecule or in the affinity of the concomitantly displayed molecules to said target of interest. Thus, these consensus structure(s) include(s) all possible experimentally obtained variations in said molecule(s) or in the manner it or they are displayed to said target of interest (respectively).

It is yet another object of the present invention to provide a method according to any previous definition, wherein at least two libraries of PNA-encoded molecules are provided in step a), the first one having PNA-encoded molecules appended at the N-terminus and the second one having PNA-encoded molecules appended at the C-terminus.

This preferred embodiment allows having PNA-encoded molecules hybridized contiguously to a nucleotide chain, wherein the PNA-encoded molecules are very closely displayed in space.

According to the invention, libraries of PNA-encoded molecules appended at the N-terminus of PNA can be accessed by standard PNA synthesis followed by coupling of the molecule to the N-terminus. While this approach does provide N-terminus appended libraries, it does not allow these libraries to be prepared in a split and mix fashion. This requires a different approach as PNAs are typically synthesized from the C-terminus (thus precluding the co-synthesis of PNA and small molecules). To be able to synthesize the library in a split and mix fashion, the PNA must be synthesized in conjunction with the small molecules. To this end, the inventors developed a new technique which is also part of the invention. Starting with an amino acid residue bearing two orthogonal amino protected groups, said residue being linked to a resin, standard PNA synthesis can be carried out following the deprotection of the first amino group with the codon for the first element of diversity. The resin is then mixed and split and the second element of diversity is introduced. The second protecting group is then removed and the amino group is reacted with a PNA oliogomer encoding the second element of diversity carrying a chloroacetamide at the N-terminus. Such oligomers are prepared on a resin which allows the cleavage of the oligomers with all the nucleobases protected (for example Boc-protected nucleobases are compatible with 1% TFA treatment required for Sieber resin cleavage). The product of the coupling is acylated with the appropriate nucleobase to complete the PNA. While the central PNA monomer is effectively a substituted PNA fragment, it is known that substitution at that position with the L stereochemistry (i.e. the stereochemistry of a natural amino acid) is beneficial for the hybridization as it confers the appropriate helicity (Englund, E. A. & Appella, D. H. (2007) Gamma-substituted peptide nucleic acids constructed from L-lysine are a versatile scaffold for multifunctional display Angew Chem Int Ed Engl 46: 1414-8; Corradini, R., Sforza, S., Tedeschi, T., Totsingan, F. & Marchelli, R. (2007) Peptide nucleic acids with a structurally biased backbone: effects of conformational constraints and stereochemistry Curr. Top. Med. Chem. 7: 681-94).

It is still another object of the present invention to provide a method according to any one of the first four definitions, wherein all the PNA-encoded molecules are appended either at the N-terminus or the C-terminus. This embodiment allows having PNA-encoded molecules hybridized contiguously or not to a nucleotide chain, wherein said PNA-encoded molecules are more distantly displayed in space.

The invention also has for object a method according to any previous definition, wherein the PNA-encoded molecules appended at the N-terminus are obtained by a split and mix fashion, in particular by orthogonal solid-phase synthesis.

In a preferred embodiment, the method according to any previous definition is a method wherein the amplification step is carried out by PCR using a 5' primer containing a tag, a functionalized solid support having affinity for said tag and a 3' primer optionally containing a fluorophore.

The 5' primer may for example contain a biotin tag in case where said solid support is a resin functionalized with streptavidin. Other tags and functionalized solid support may be chosen by a person skilled in the art. The fluorophore may be used for microarray readout.

The invention also has for object a method of preparing an adduct as potential drug candidate or catalyst, said method comprising the method according to any previous definition, further comprising the following steps:
  i) synthesizing a covalent adduct mimicking the consensus structure,
  j) validating the biological or catalytic activity of the covalent adduct.

FIGS. 1 to 10 and examples 1 to 11 illustrate the invention.

FIG. 1 illustrates the general concept of the invention. Libraries of PNA-encoded small molecules (represented by the triangle and parallelogram shapes) are assembled combinatorially onto a library of DNA template. The mixture is screened by panning over an immobilized target and the DNA corresponding to the fittest ligand combination is amplified. The selection/amplification can be repeated for several cycles and then the DNA is sequence and the covalent version of the small molecule fragments is prepared.

FIG. 2 is a schematic representation of a DNA-Templated Self-Assembled Library (DTSAL). Libraries are prepared by well established PNA-encoded split and mix combinatorial synthesis (a library of benzodiazepines is used arbitrarily to denote a general library). Libraries containing different pharmacophore fragments are then self-assembled according to the rules of hybridization onto a DNA template library containing all combinations of complementary sequences (for clarity and simplicity, the primers of the DNA template are not shown).

Figure 8:
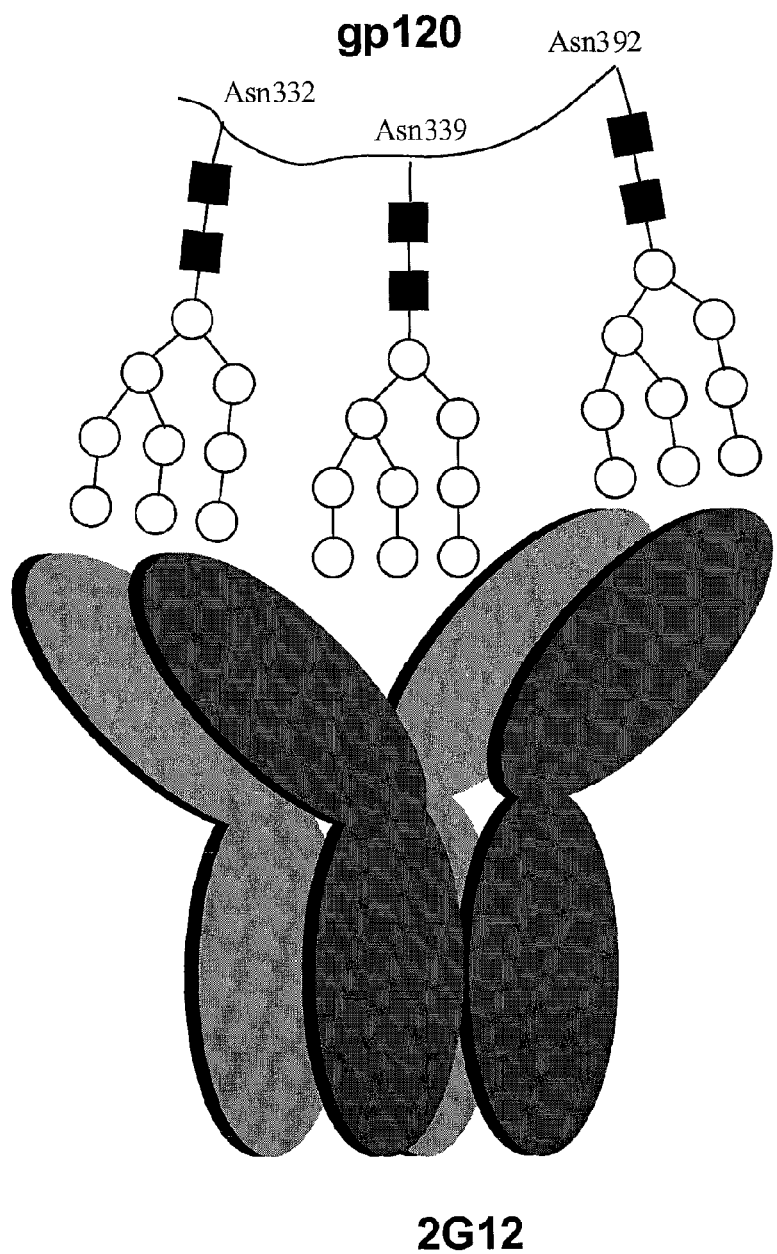

FIG. 8 represents the proposed binding mode of 2G12 dimer with gp120 according to D. A. Calarese, C. N. Scanlan, M. B. Zwick, S. Deechongkit, Y., Mimura, R. Kunert, P. Zhu, M. R. Wormald, R. L. Stanfield, K. H. Roux, J. W. Kelly, P. M. Rudd, R. A. Dwek, H. Katinger, D. R. Burton, I. A. Wilson, Science 2003, 300, 2065-2071.

Figure 9:
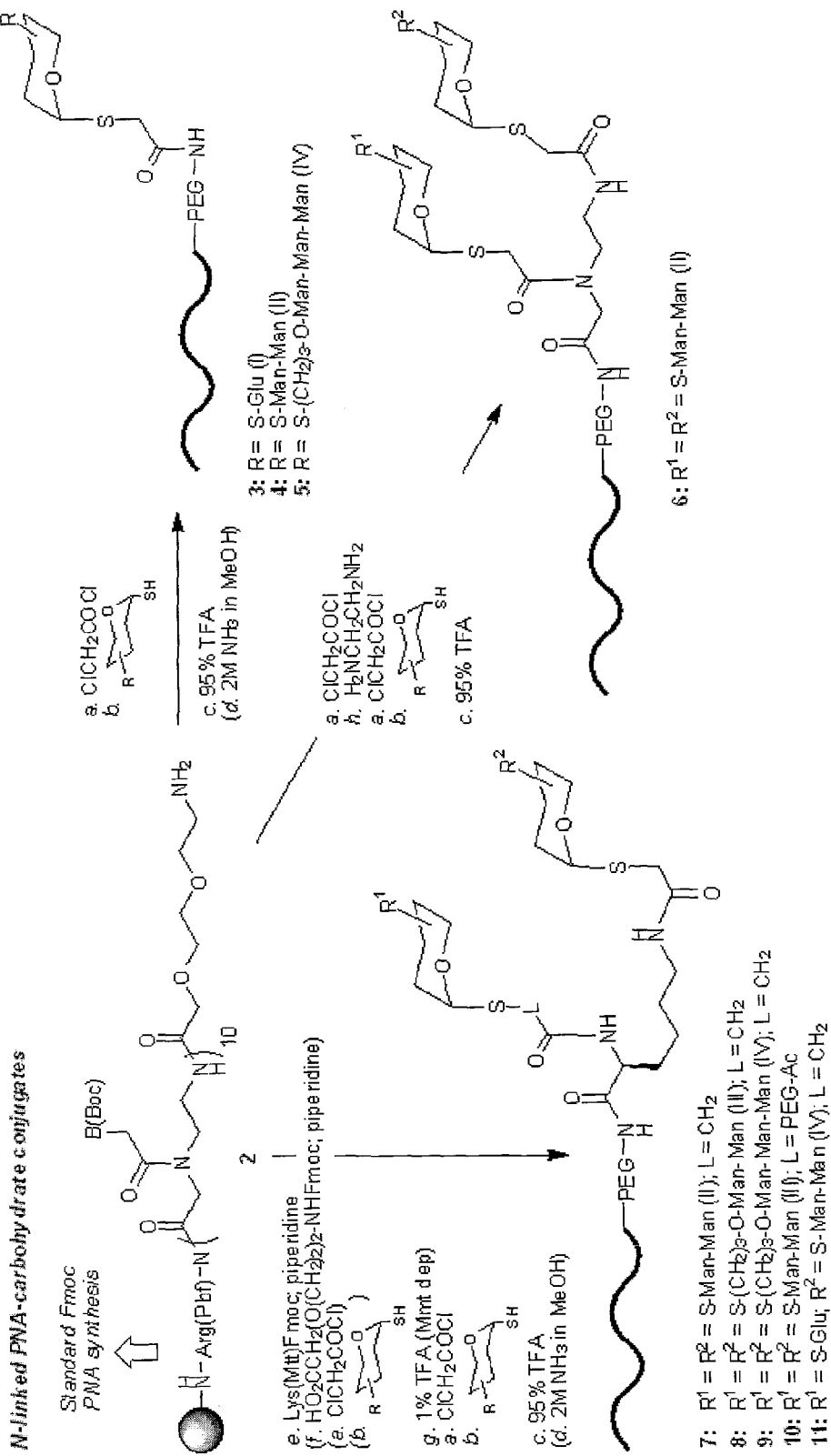
Figure 9:
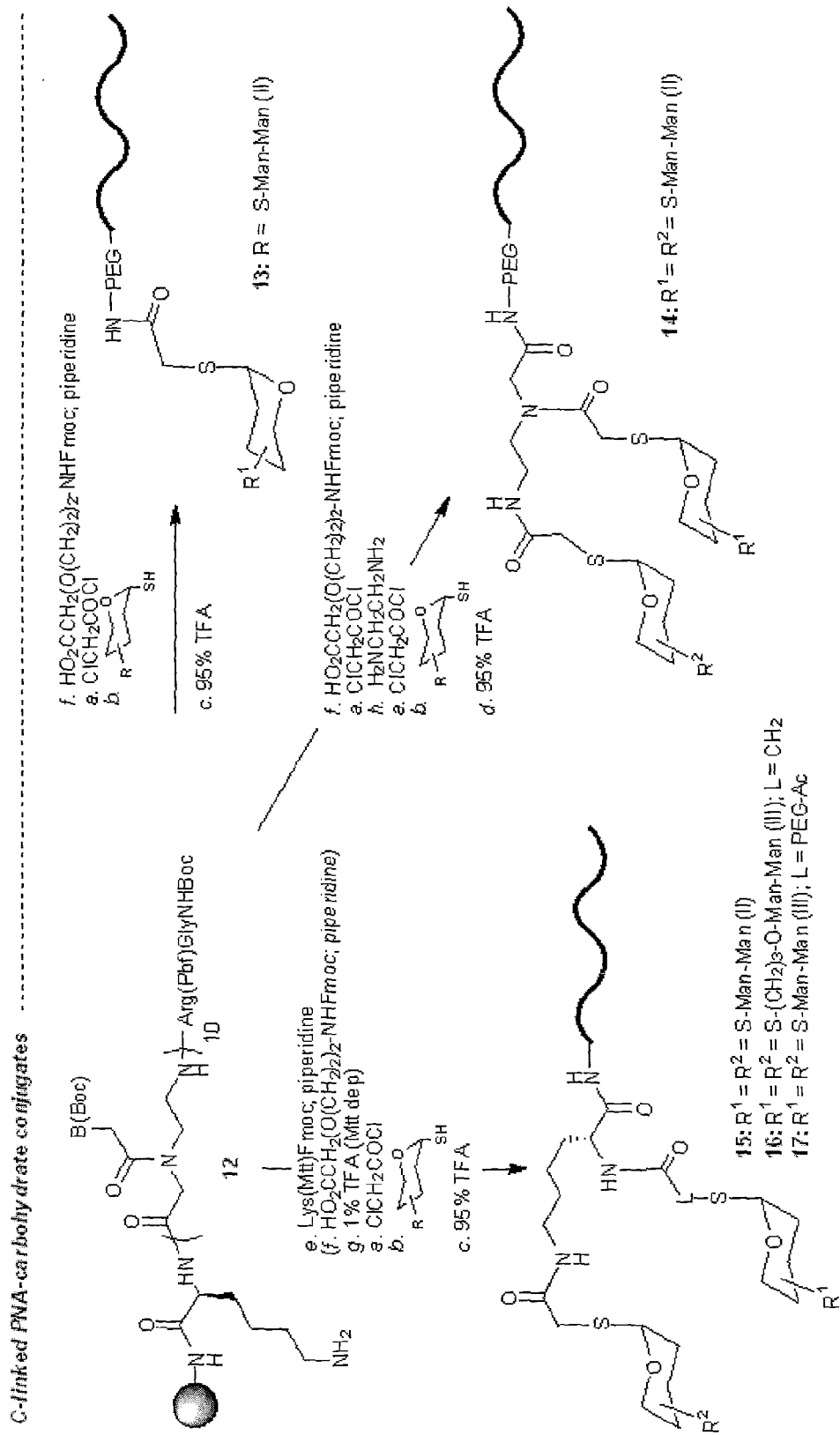
Figure 9:
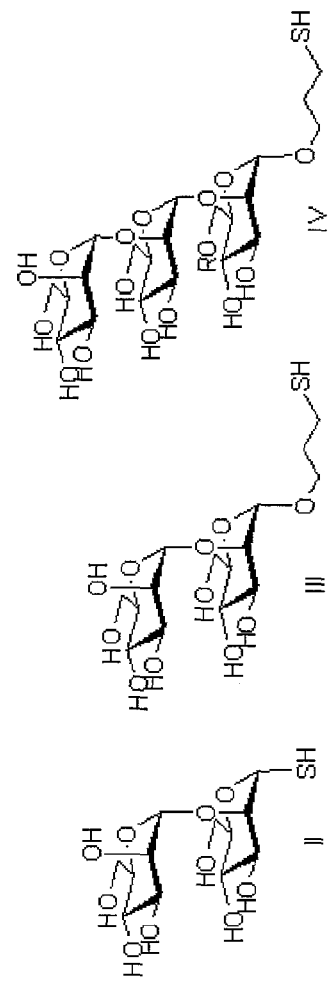
Figure 9:
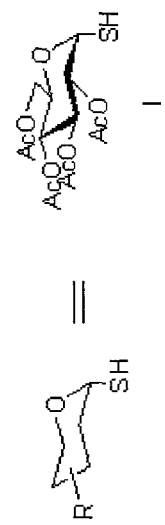

FIG. 9 represents the synthesis of N- and C-linked PNA carbohydrate conjugates according to example 8.

Figure 10:
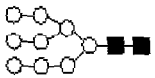
Figure 10:
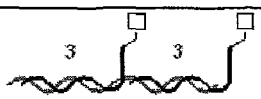
Figure 10:
Figure 10:
Figure 10:
Figure 10:
Figure 10:
Figure 10:
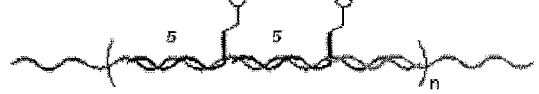
Figure 10:
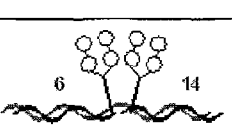
Figure 10:
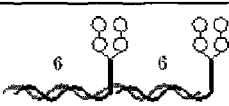
Figure 10:
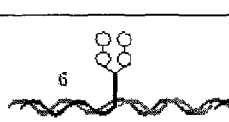
Figure 10:
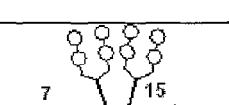
Figure 10:
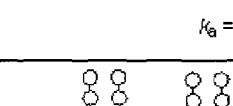
Figure 10:
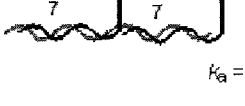
Figure 10:
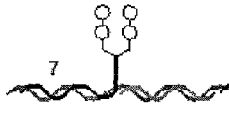
Figure 10:
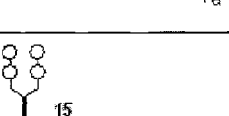
Figure 10:
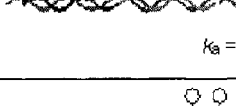
Figure 10:
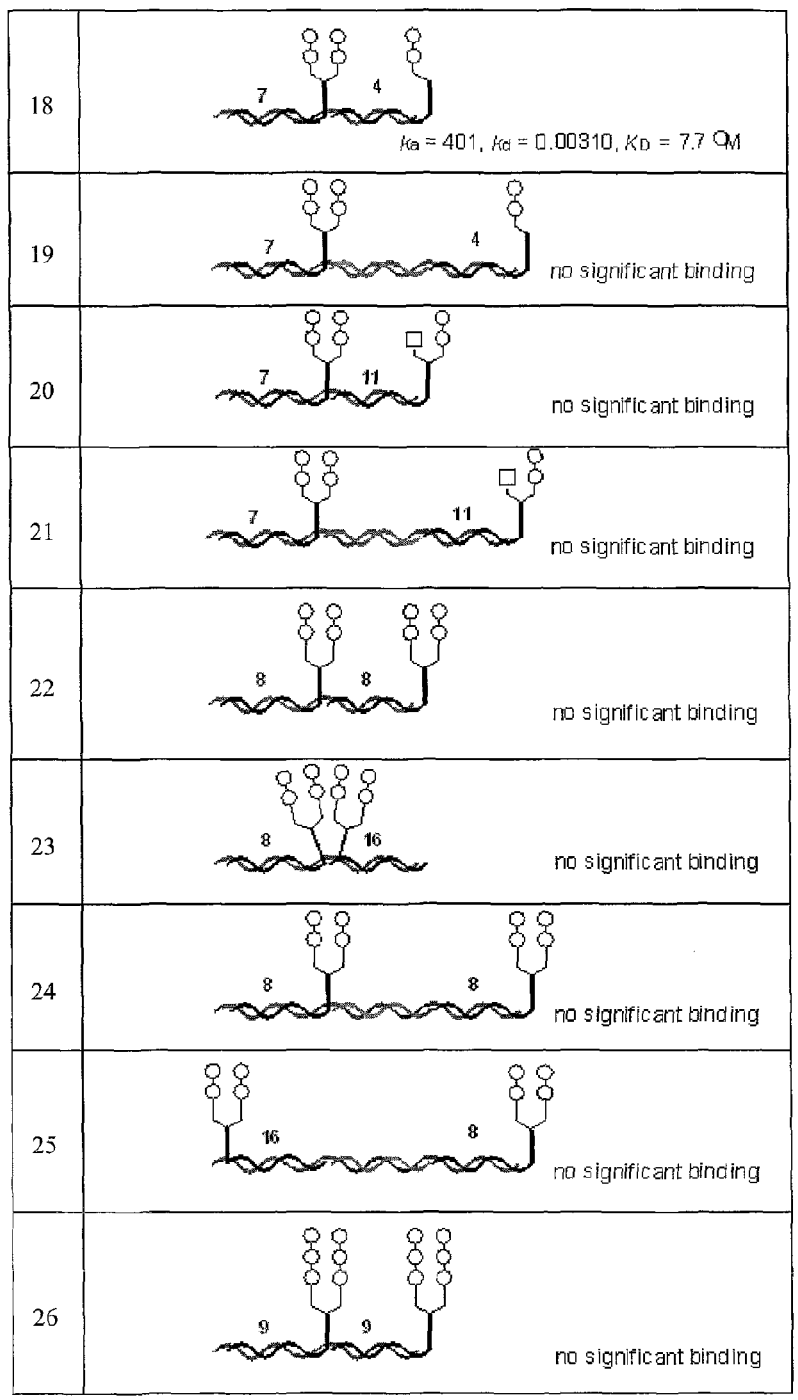
Figure 10:
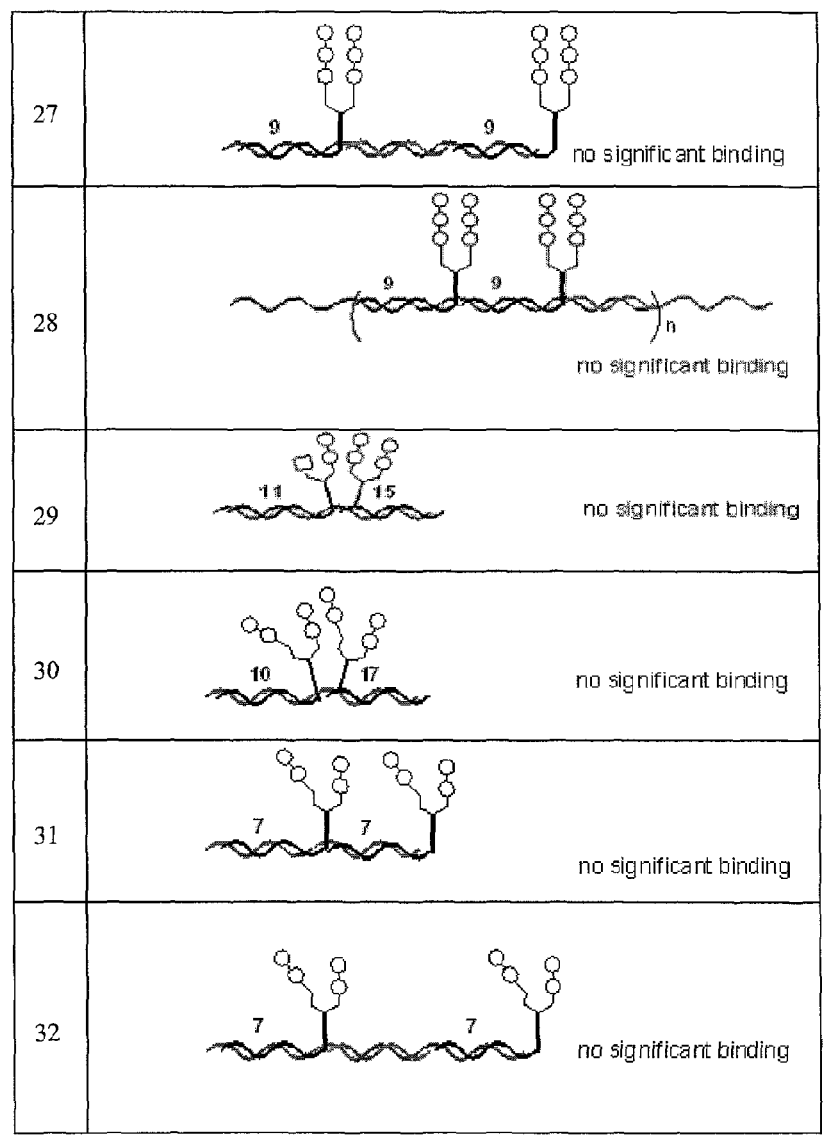

FIG. 10 shows the affinity of supramolecular complexes to 2G12 measured by SPR (ka is (1/Ms) and kd is (1/s)) according to example 10. Solutions were prepared by mixing 1 equivalent of each PNA with their respective template (*concentration of the template).

EXAMPLE 1

General Concept of the Invention

Figure 1:
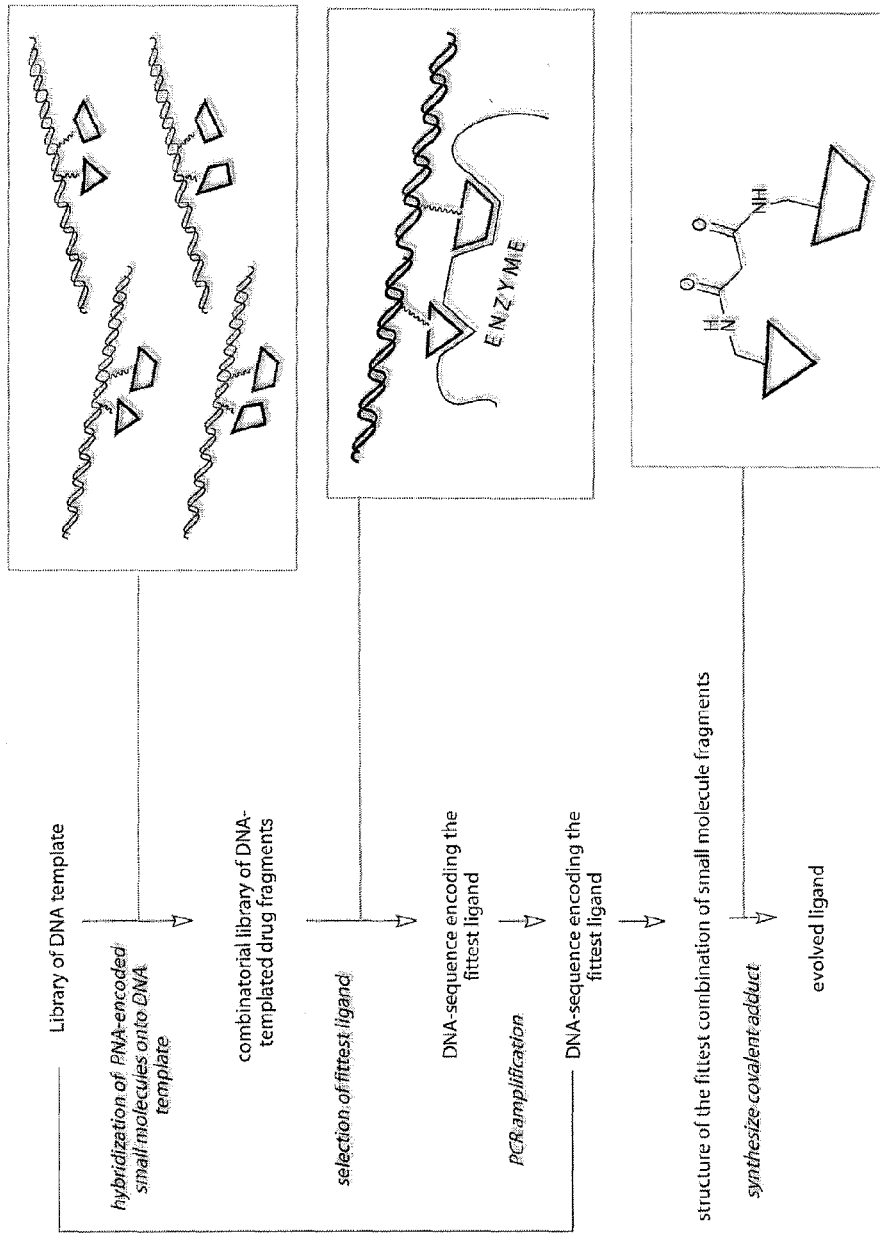
Figure 2:
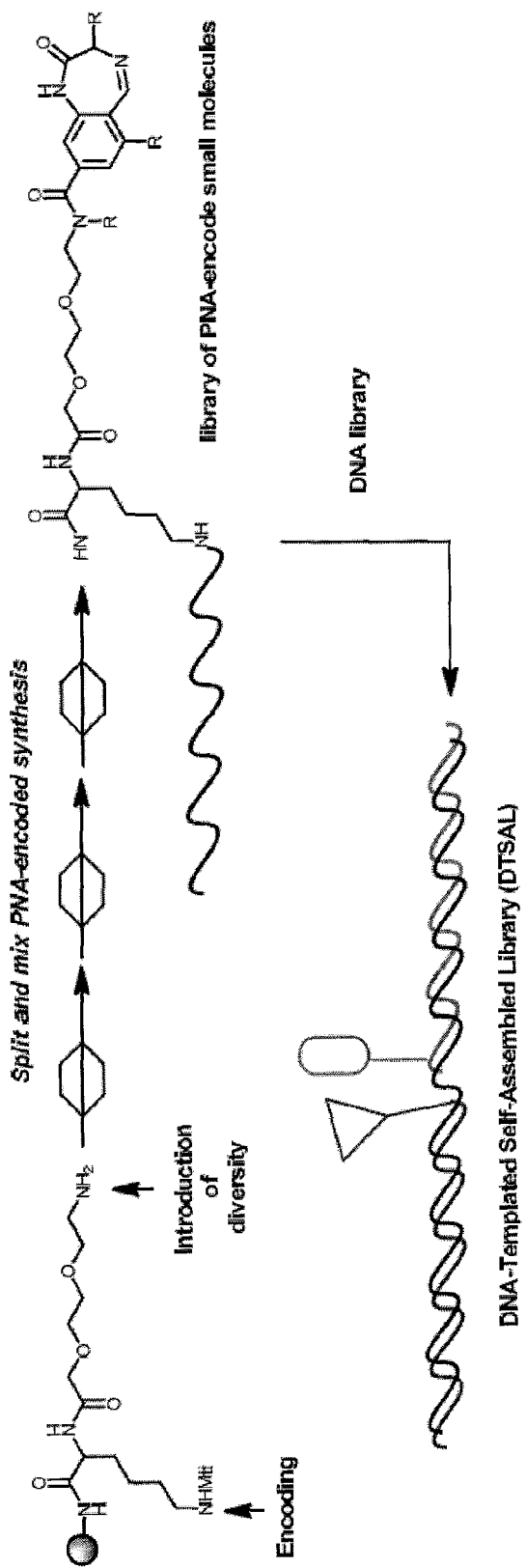

Two libraries of PNA-encoded molecules represented by the triangle and parallelogram shapes on the FIG. 1 and chosen among, for example peptides, peptoids, heterocycles or natural product derivatives, are self assembled onto a library of DNA templates (obtained by split and mix combinatorial synthesis). The library is then incubated with a molecule of interest and the fittest ligand is retained by affinity (the protein may for example be immobilized on magnetic beads or on a surface such as an surface-plasmon resonance sensor chip). The identity of the fittest ligand can be decoded by PCR amplification of the DNA template. Additionally, the PCR product can be immobilized by using a PCR-primer with a tag (such as biotin) and converted to a single strand such that the PNA-encoded library can be rehybridized. Since the DNA-template will only have complimentary sequences for the molecules that were selected, the rest of the library will flow through. Releasing the DNA template into solution thus affords a library containing only the molecules which were selected and this library can be used for a second round of sequencing. Reiteration of this process should refine the best ligand. It is important to note that the rehybridization step allows for "mutation" to be incorporated by introducing different PNA-encoded libraries bearing different substitutions.

EXAMPLE 2

General Synthesis Techniques

All reactions were carried out under a nitrogen atmosphere with dry (anhydrous) solvents under anhydrous conditions, unless otherwise noted Anhydrous solvents were obtained by passing them through commercially available alumina column (Innovative Technology, Inc.,® VA). NovaPEG Rink Amide Resin resin was purchased from Novabiochem®, and was swollen in DCM before each reaction. Solid phase reactions were carried in SPE tubes fitted with a frit and a tap. Automated solid phase synthesis was carried out on an Intavis Multipep instrument (http://www.intavis.com/en/Automated_Peptide_Synthesis/MultiPep_RS/index.php). LC-MS were recorded using an HP 1100 series or Thermo Electron Corporation HPLC with a Thermo Finnigan Surveyor® MSQ Mass Spectrometer System. A Thermo Scientific column (50×2.1 mm) was used. MALDI spectra were measured using a Brucker Daltonics Autoflex™ II TOF/TOF spectrometer. Polymer-bound intermediates were characterized by LC-MS and/or MALDI (2,5-Dihydroxybenzoic acid or a-Cyano-4-hydroxycinnamic acid matrix and desorbed with laser between 35-55%) following a cleavage from the resin. Cleavages were carried out on 0.1-0.3 mg of dry resin with 20 µL of TFA for 20 min at room temperature. The TFA solution was either evaporated or added to 200 µL of $Et_2O$ and centrifuged at 18000 g for 5 min to pellet the precipitated compound. The resulting white pellet was then washed with $Et_2O$ (200 µL) and redisolved in 1:1 $MeCN:H_2O$ (404) for analysis. The mix and split synthesis was performed according to previously established protocols (J. L. Harris, N. Winssinger *J. Eur. Chem.* 2005, 11, 6792-6801; F. Debaene, J. DaSilva, Z. Pianowski, F. Duran, N. Winssinger *Tetrahedron* 2007, 63, 6577-6586).

General Procedures for the Synthesis of PNA-Encoded Libraries

Procedure 1: General Procedure for Capping the Resin

To 100 mg of NovaPEG Rink amide resin 2.0 mL of capping mixture (9.2 mL of acetic anhydride and 13 mL of 2,6 lutidine in 188 mL of DMF) were added, and the resin was shaken for 15 min. Subsequently, the resin was washed with 6×2 mL of DMF and 6×2 mL of $CH_2Cl_2$.

Procedure 2: General Procedure for Capping in Intavis AG Multipep RS Synthesizer To 10 mg of NovaPEG Rink amide resin were added 100 µL of capping mixture (9.2 mL of acetic anhydride and 13 mL of 2,6 lutidine in 188 mL of DMF). After 5 min, the resin was washed with 2×250 µL of DMF.

Procedure 3: General Procedure for Fmoc Deprotection

To 100 mg of NovaPEG Rink amide resin were added 2.0 mL of 20% piperidine solution in DMF, and the resin was shaken for 5 min. Subsequently, the resin was washed with 6×2 mL of DMF and 6×2 mL of $CH_2Cl_2$, and the deprotection sequence was repeated a second time.

Procedure 4: General Procedure for Fmoc Deprotection in Intavis AG Multipep RS Synthesizer To 10 mg of NovaPEG Rink amide resin were added 100 µL of 20% piperidine solution in DMF. After 2 min, the resin was washed with 250 µL DMF and the sequence was repeated a second time. Finally, the resin was washed with 5×250 µL of DMF and 3×250 µL of $CH_2Cl_2$.

Procedure 5: First Lysine Coupling on Resin, Loading Reduction

To a solution of 56.2 mg (0.09 mmol, 1.0 equiv, 0.2 mmol/g loading) of Fmoc-Lys(Mtt)-OH in 7.0 mL of NMP were added 68.9 mg (0.45 mmol, 5 equiv) of HOBt followed by 210 µL of DIC. The mixture was stirred for 5 min at room temperature, and then added to 450 mg of NovaPEG Rink amide resin. The reaction mixture was shaken for 16 hours and subsequently the resin was washed with 6×10 mL of DMF and 6×10 mL of $CH_2Cl_2$.

Procedure 6: PEG-Spacer Coupling

To a solution of Fmoc protected-PEG spacer (4.0 equiv) in NMP (60 mM) were added (3.5 equiv) of HCTU NMP (0.5M) followed by base solution [DIPEA 1.2 M (0.25 mmol, 4 equiv) and 2,6 lutidine 1.8M (0.38 mmol, 6.0 equiv) in NMP]. The mixture was stirred for 5 min at room temperature, and then added to the pre-swollen resin. The reaction mixture was shaken for 16 hours and subsequently the resin was washed with 6×DMF and 6×$CH_2Cl_2$. Finally, the resin was capped (procedure 1) and Fmoc was deprotected (procedure 3).

Procedure 7: General Procedure for Amino Acid Coupling to Resin in Intavis AG Multipep RS Synthesizer To a solution of 8.0 mmol (4.0 equiv) of Fmoc protected aminoacid in 40 µL of NMP were added 14 µL (7.0 mmol, 3.5 equiv) of HCTU 0.5 M in NMP, followed by 6.7 µL of base solution (DIPEA 1.2 M (0.008 mmol, 4.0 equiv) and 2,6 lutidine 1.8 M (0.012 mmol, 6.0 equiv) in NMP). The mixture was then added to 10 mg (2.0 mmol, 1.0 equiv) of the corresponding resin. After 20 min the resin was filtered and washed with DMF and the sequence was repeated. The resin was then filtered and washed with 6×250 µL of DMF and 6×250 µL of $CH_2Cl_2$. Finally, the resin was capped (procedure 2, 100 µL) and Fmoc was deprotected according to procedure 4 (100 µL).

Procedure 8: General Procedure for the Azide Generation

To a solution of 294 mg (1.4 mmol, 11 equiv) imidazole-1-sulfonyl azide hydrochloride in 12.6 mL of MeOH were added successively 305 mg (2.2 mmol, 18 equiv) $K_2CO_3$ and 8.0 mg (0.05 mmol, 0.35 equiv) anhydrous $CuSO_4$ and the resulting solution was sonicated for 20 min. To 10 mg (2.0 mmol, 1.0 equiv) of the corresponding resin were added 250 µL of previously prepared solution. After 16 hours, the resin was washed with 6×250 µL of sodium diethyl dithiocarbamate 0.02 M in DMF, 6×250 µL of DMF, 6×MeOH and 6×$CH_2Cl_2$, and the sequence was repeated again.

Procedure 9: Mtt Deprotection on NovaPEG Resin in Intavis AG Multipep RS Synthesizer To 10 mg of resin (0.2 mmol, 1.0 equiv) were added 250 µL of 50% hexafluoroisopropanol in DCE which was allowed to drip though resulting in an exposure of 30 sec. The process was repeated 5 times then the resin was washed with 2×250 µL $CH_2Cl_2$ and 4×2504 of DMF.

Procedure 10: General Procedure for PNA Synthesis on NovaPEG Resin in Intavis AG Multipep RS Synthesizer To a solution of 8.0 µmol (4.0 equiv) of the corresponding Fmoc or Mtt—protected PNA monomer (the nucleobased are Boc protected—S. Pothukanuri, Z. Pianowski, N. Winssinger, Eur. J. Org. Chem., 2008, 18, 3141-48) in 40 µL of NMP were added 14 µL (7.0 mmol, 3.5 equiv) of HATU 0.5M in NMP, followed by 6.7 µL of base solution [DIPEA 1.2 M (0.008 mmol, 4.0 equiv) and 2,6 lutidine 1.8M (0.012 mmol, 6.0 equiv) in NMP]. The mixture was then added to 10 mg of the corresponding resin. After 20 min the resin was filtered and washed with DMF and the sequence was repeated, then, the resin was washed with 6×10 mL of DMF and 6×10 mL of $CH_2Cl_2$. Finally, the resin was capped (procedure 2) and Fmoc was deprotected according to procedure 4 or Mtt deprotection according to procedure 9.

Procedure 11: General Procedure for Cleavage of Compounds from the Resin

The resin was treated with TFA (95% in $H_2O$) for 4 hours. The TFA solution was precipitated in $Et_2O$ (10 times TFA volume) and centrifuged to recover the product as a pellet. The precipitate was re-dissolved in $H_2O$ (500 mL for crude cleaved from 10 mg of resin) then lyophilized.

Procedure 12: General Procedure for Click Cycloaddition Reaction on NovaPEG Resin in Intavis AG Multipep RS Synthesizer To the corresponding resin (~10 mg) were added successively 173 µL (0.0173 mmol, 7.5 equiv) of alkyne 0.1M in NMP, 17.3 µL (17.2 mmol, 7.5 equiv) of sodium ascorbate 198 mg/mL in $H_2O$, 4.4 µL (0.57 mmol, 0.25 equiv) of copper sulfate 21.4 mg/mL in $H_2O$ and 44 µL (1.1 mmol, 0.5 equiv of TBTA). After 16 hours, the resin was washed with 6×250 µL of sodium diethyl dithiocarbamate 0.02 M in DMF, 6×250 µL of DMF, 6×MeOH and 6×$CH_2Cl_2$.

Procedure 13: General Procedure for the Loading of the Flavones

The resin was swelled in $CH_2Cl_2$ for 20 min and treated with a premixed (30 min) solution of the corresponding flavon (5.0 equiv), HOBt (5.0 equiv), DIC (15 equiv) in NMP (1 mL) during 5 hours. Then the resin was filtered and washed with 6×10 mL of DMF and 6×10 mL of $CH_2Cl_2$.

Procedure 14: General Procedure for the Reactions with Hydrazine or Amidinium Salt The resin (1.0 equiv) was treated with a premixed solution of the corresponding hydrazine or amidinium salt (3.0 equiv) and a aqueous solution of $NaHCO_3$ (3M, 4.0 equiv) in nBuOH (0.5 mL), and then was shaken at 50° C. for 18 hours. The mixture was filtered and washed sequentially with DMF and $CH_2Cl_2$.

Procedure 15: General Procedure for the Reduction of the Azide

The resin (10 mg, 2 µmol, 1.0 equiv) was treated with a 1M solution of $PMe_3$ (3.0 equiv, THF) in THF (200 mL) for 5 min. After, $H_2O$ (200 mL) was added and the reaction was shaken for 8 hours. The resin was washed with THF, $H_2O$ and finally with DMF and $CH_2Cl_2$.

Procedure 16: General Procedure for Chloroacetamide Formation

The resin (10 mg, 2 µmol, 1.0 equiv) was swollen in $CH_2Cl_2$ for 20 min and deprotected with 20% piperidine in DMF (200 μL) for 10 min; then it was washed with DMF and $CH_2Cl_2$ and treated with a premixed solution of chloroacetic anhydride (6.8 mg, 20 equiv) and 2,6-lutidine (5.2 μL, 22.5 equiv) in $CH_2Cl_2$ (150 μL) for 15 minutes. This process was repeated twice. The resin was then washed with DMF and $CH_2Cl_2$.

EXAMPLE 3

Synthesis of a 500 Membered Triazole Library

First Point of Diversity 25 Different Aminoacids
NovaPEG Rink amine resin (500 mg) was loaded with FmocLys(Mtt)OH procedure 5 following by capping of the un-reacted amine groups (procedure 1). Fmoc deprotection (procedure 3), loading of the spacer (procedure 6) and second Fmoc deprotection (procedure 3) yielded a resin that was split on to 30 different columns (10 mg of resin per column) for the loading of 30 different aminoacids from table 1 in the Multi-pep Synthesizer (procedure 7 followed by procedure 4). Then, following procedure 8 the Fmoc deprotected amino acids were converted to the corresponding azides. The orthogonal Mtt protecting group on the side chain of the Lys was then deprotected using procedure 9 and corresponding 7-mers PNA were synthesized following procedure 10.

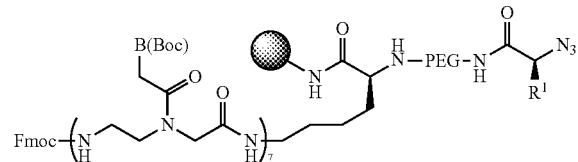

$R^1$ represents a residue of one amino acid of table 1.

TABLE 1

Amino-acids used as elements of diversity

| Entry | Aminoacid | m/z calcul | m/z found |
|---|---|---|---|
| 1 | (2S,3S)-2-amino-3-methoxybutanoic acid | 2686.54 | 2687.04 |
| 2 | (S)-2-amino-3-methoxypropionic acid | 2617.53 | 2617.26 |
| 3 | Ala | 2611.48 | 2611.96 |
| 4 | allo-Thr | 2641.50 | 2642.52 |
| 5 | Arg | 2712.59 | 2713.13 |
| 6 | Asn | 2733.55 | 2734.95 |
| 7 | D-Phe | 2711.59 | 2712.13 |
| 8 | Gln | 2716.55 | 2716.69 |
| 9 | Glu | 2717.55 | 2718.02 |
| 10 | Gly | 2661.47 | 2661.99 |
| 11 | His | 2708.54 | 2709.62 |
| 12 | Homoser | 2617.49 | 2618.06 |
| 13 | L-4-Pyridylalanine | 2688.54 | 2689.13 |
| 14 | L-beta-t-butylalanine | 2667.58 | 2668.16 |
| 15 | L-cyclopropylglycine | 2653.51 | 2653.93 |

TABLE 1-continued

Amino-acids used as elements of diversity

| Entry | Aminoacid | m/z calcul | m/z found |
|---|---|---|---|
| 16 | Leu | 2732.58 | 2733.07 |
| 17 | Ile | 2677.57 | 2678.61 |
| 18 | Lys | 2717.54 | 2717.11 |
| 19 | Nle | 2701.56 | 2701.56 |
| 20 | Phe | 2751.58 | 2752.05 |
| 21 | Ser | 2666.48 | 2667.02 |
| 22 | Thr | 2625.54 | 2625.98 |
| 23 | Trp | 2735.62 | 2736.02 |
| 24 | Tyr | 2711.59 | 2712.10 |
| 25 | Val | 2663.55 | 2663.55 |

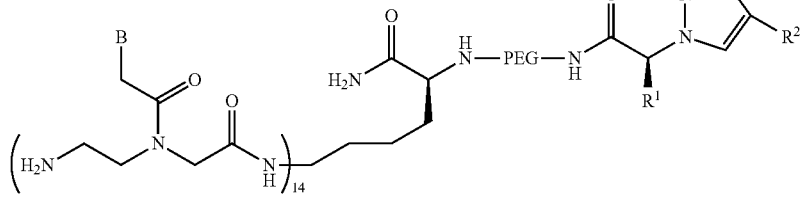

$R^1$ represents a residue of one amino acid of table 1 and $R^2$ an alkynyle residue according to table 2.

Second Point of Diversity 25 Different Alkynes

The resin from the previous reactions (20 cleanest products) were combined, thoroughly mixed and redistributed into 20 columns. Resin transfers were carried out as slurry in DCM/DMF using pipetting.

After click cycloaddition reaction with one alkyne of table 2 per column was done following procedure 12 the second PNA codon (7mer) was introduced following procedure 10. The success of the reactions in each pool was assessed by MALDI showing complete conversions.

TABLE 2

Alkyne used as elements of diversity

| Entry | Alkyne | m/z (M + Na$^+$) range |
|---|---|---|
| 1 | 4-Ethynylanisole | 4717.31-4857.42 |
| 2 | 1-Ethynyl-2-methoxybenzene | 4757.32-4897.43 |
| 3 | 2-Ethynylaniline | 4718.30-4858.41 |
| 4 | 1-Ethynyl-4-phenoxybenzene | 4795.38-4935.49 |
| 5 | N-Methyl-N-propargylbenzylamine | 4713.39-4853.50 |
| 6 | 3-Ethynylanisole | 4726.33-4866.44 |
| 7 | 3-Cyclohexyl-1-propyne | 4692.36-4832.47 |
| 8 | 3-Dimethylamino-1-propyne | 4653.28-4793.39 |
| 9 | 2-Methyl-3-butyn-2-ol | 4638.28-4778.39 |
| 10 | 4-Ethynylaniline | 4711.32-4851.43 |
| 11 | 3-Butyn-1-ol | 4640.24-4780.35 |
| 12 | 3-Butyn-2-ol | 4640.24-4780.35 |
| 13 | Phenyl propargyl ether | 4686.32-4826.43 |
| 14 | Cyclopropylacetylene | 4660.27-4800.38 |
| 15 | 4-Pentyn-1-ol | 4654.27-4794.38 |
| 16 | N-Propargylphthalimide | 4755.33-4895.44 |
| 17 | 3-Hydroxyphenylacetylene | 4672.29-4812.40 |
| 18 | 3-Ethynylaniline | 4711.32-4851.43 |
| 19 | Phenylacetylene | 4672.28-4812.39 |
| 20 | 1-heptyne | 4666.32-4806.43 |

EXAMPLE 4

Synthesis of a 500 Membered Pyrimidines and Pyrazoles Library

First Point of Diversity, 5 Different Aminoacids

NovaPEG Rink amine resin (500 mg) was loaded with FmocLys(Mtt)OH procedure 5 following by capping of the un-reacted amine groups (procedure 1). Fmoc deprotection (procedure 3), loading of the spacer (procedure 6) and second Fmoc deprotection (procedure 3) yielded a resin that was split on to 5 different columns (50 mg of resin per column) for the loading of 5 different amino acids in the Multipep Synthesizer (procedure 7 followed by procedure 4). Then, following procedure 8 the Fmoc deprotected amino acids were converted to the corresponding azides. The orthogonal Mtt protecting group on the side chain of the Lys was then deprotected using the protocol decipher in procedure 9 and corresponding 4-mers were loaded onto all the five different resins following procedure 10. Maldi analysis of an analytical cleavage from each pool confirmed the completion of each sequence.

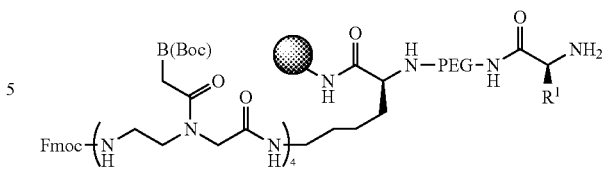

$R^1$: Phe, Val, Leu, Ala, Ile.

Second Point of Diversity, 5 Different Flavones

The 5-resins prepared in the previous step were suspended in 0.5 mL $CH_2Cl_2$ and mixed together in a SPE tube. The resin was shaken for 30 minutes, washed with 2×$CH_2Cl_2$ and then the resin was distributed in 5 different columns in the Multipep Synthesizer. Then the azide group was reduced following procedure 15 and each of the resins was coupled to a different flavon (procedure 13) and capped (procedure 2). PNA encoding according to procedure 11 was then carried out.

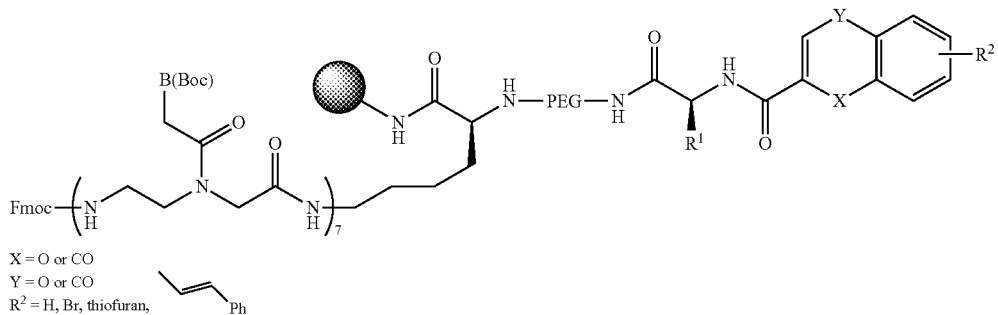

$R^1$ represents Phe, Val, Leu, Ala, Ile $R^2$ represents the different flavones used and are defined in table 4.

TABLE 3

| | | | | m/z (M + Na⁺) | m/z (M + Na⁺) |
|---|---|---|---|---|---|
| Entry | Flavon | | CODON | calcul | found |
| 1 | HO₂C flavon structure | | T*GG | Phe: 2661.53<br>Val: 2691.43<br>Leu: 2693.42<br>Ala: 2691.44<br>Ile: 2691.43 | Phe: 2661.92<br>Val: 2692.99<br>Leu: 2694.42<br>Ala: 2692.99<br>Ile: 2692.99 |
| 2 | HO flavon structure | | C*CG | Phe: 2661.51<br>Val: 2661.43<br>Leu: 2774.41<br>Ala: 2680.43<br>Ile: 2762.43 | Phe: 2661.92<br>Val: 2662.09<br>Leu: 2776.42<br>Ala: 2681.43<br>Ile: 2763.41 |
| 3 | HO₂C flavon with Br | | G*CA | Phe: 2930.42<br>Val: 2811.34<br>Leu: 2877.32<br>Ala: 2883.34<br>Ile: 2885.34 | Phe: 2931.93<br>Val: 2813.35<br>Leu: 2878.32<br>Ala: 2883.24<br>Ile: 2886.35 |

Table header note: "Flavons used as element of diversity"

TABLE 3-continued

Flavons used as element of diversity

| Entry | Flavon | CODON | m/z (M + Na$^+$) calcul | m/z (M + Na$^+$) found |
|---|---|---|---|---|
| 4 | HO$_2$C-[flavon with styryl-Ph substituent] | C*GA | Phe: 2834.62<br>Val: 2874.64<br>Leu: 2890.62<br>Ala: 2906.54<br>Ile: 2908.64 | Phe: 2832.56<br>Val: 2874.54<br>Leu: 2891.45<br>Ala: 2905.54<br>Ile: 2909.54 |
| 5 | HO$_2$C-[flavon with thiophene substituent] | G*GC | Phe: 2930.617<br>Val: 2930.5394<br>Leu: 2896.517<br>Ala: 2892.539<br>Ile: 2894.6332 | Phe: 2932.312<br>Val: 2931.235<br>Leu: 2897.613<br>Ala: 2892.543<br>Ile: 2895.654 |

* means a modified PNA (GPNA) according to Imaging of mRNA in Live Cells Using Nucleic-Acid Templated Reduction of Azidorhodamine Probes, Z. Pianowski, K. Gorska, L. Oswald, C. A. Merten, N. Winssinger, *J. Am. Chem. Soc.*, 2009, 6492-6497.

Third Point of Diversity, 20 Different Hydrazines or Amidinium Salts

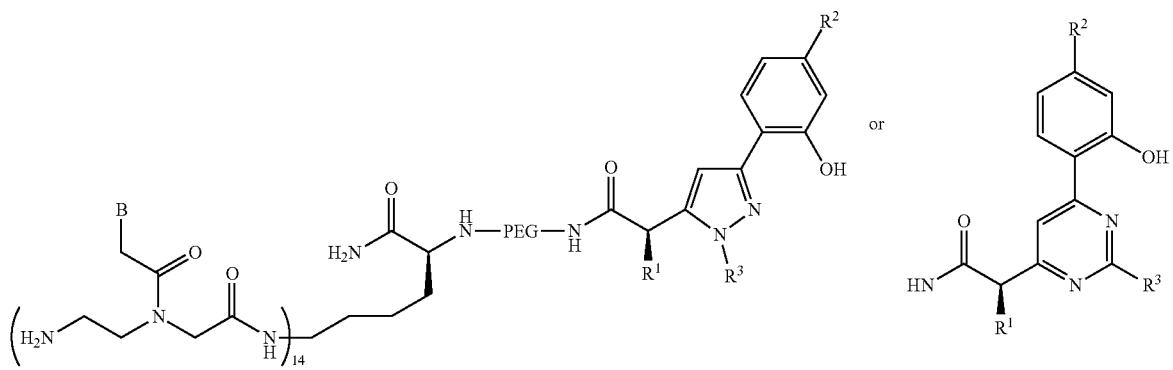

$R^1$ and $R^2$ were defined in table 2 and 3 respectively, $R^3$ represents the different hydrazines and amidinium salts used and are defined in table 4.

The five resin pools were mix in a 12 mL tube and swelled with CH$_2$Cl$_2$ (20 min) and split in 20 columns in the Multipep Synthesizer (12.5 mg). The corresponding amidine or hydrazine from table 4 was coupled following procedure 15 and after Fmoc deprotection (procedure 4) the corresponding 7mers were couple following procedure 10. Final Fmoc deportection (procedure 4) and cleavage of the compounds from the resin (procedure 11) gave 20 different pools. Each pool was analyzed by MALDI to confirm the completion of the reaction sequence.

TABLE 4

Amidine or hydrazine used as elements of diversity

| Entry | Hydrazine/amidine | m/z (M + Na$^+$) calcul. range | m/z (M + Na$^+$) found | CODON |
|---|---|---|---|---|
| 1 | Hydrazine | 4984.37-5140.50 | 4998.5-5249.17 | GTGCGAA |
| 2 | Methylhydrazine | 5038.39-5198.63 | 5050.34-5200.43 | GTGGAGA |
| 3 | Hydroxilamine | 5001.35-5161.59 | 5010.23-5176.33 | GTGCAGG |
| 4 | 2-Hydrozinopyridine | 5099.39-5257.63 | 5100.22-5260.13 | GTGGACG |
| 5 | Hydralazine | 5097.41-5257.64 | 5099.22-5288.01 | GCAAGGC |
| 6 | p-Tolylhydrazine | 5043.42-5203.66 | 5050.22-5205.11 | GCACGAA |
| 7 | 4-tButylhydrazine | 5131.47-5291.70 | 5129.43-5300.21 | GCAGAGA |
| 8 | 4-Nitrophenylhydrazine | 5090.38-5250.62 | 5100.23-5260.33 | GCACAGG |
| 9 | 4-Hydrazinobenzoic acid | 5089.39-5249.62 | 5090.22-5250.99 | ACGGACG |
| 10 | 3-(Trifluoromethyl)phenylhydrazine | 5113.39-5273.62 | 5110.88-5285.44 | ACGAGGC |
| 11 | 2-Ethylphenylhydrazine | 5057.14-5217.37 | 5060.33-5216.44 | ACGCGAA |

TABLE 4-continued

Amidine or hydrazine used as elements of diversity

| Entry | Hydrazine/amidine | m/z (M + Na+) calcul. range | m/z (M + Na+) found | CODON |
|---|---|---|---|---|
| 12 | 3,4-Dimethylphenyl-hydrazine | 5097.45-5257.68 | 5100.22-5260.44 | ACGGAGA |
| 13 | 4-Chloro-o-tolyl-hydrazine | 5094.07-5254.30 | 5098.33-5253.99 | CGACAGG |
| 14 | Acetamidine | 4995.54-5155.77 | 4998.33-5160.33 | CGAGACG |
| 15 | Benzamidine | 5057.40-5217.63 | 5060.33-5210.44 | CGAAGGC |
| 16 | 3-Aminobenzamidine | 5056.63-5216.87 | 5070.33-5210.33 | CGACGAA |
| 17 | 4-Aminobenzamidine | 5096.64-5256.88 | 5098.22-5254.66 | AGCGAGA |
| 18 | 2-(Phenylthio)ethan-imidamide | 5071.41-5231.65 | 5077.22-5230.55 | AGCCAGG |
| 19 | 3-methylbenzamidine | 5038.39-5198.62 | 5035.44-5199.22 | AGCGACG |
| 20 | Malonamidine | 5043.22-5100.23 | 5042.33-5102.33 | AGCAGGC |

EXAMPLE 5

Coupling of Pharmacophore to the N-Terminus of PNA

PNA prepared according to the procedure 10 were derivatized with commercially available pharmacophore by coupling of an acid, alcohol or amine.

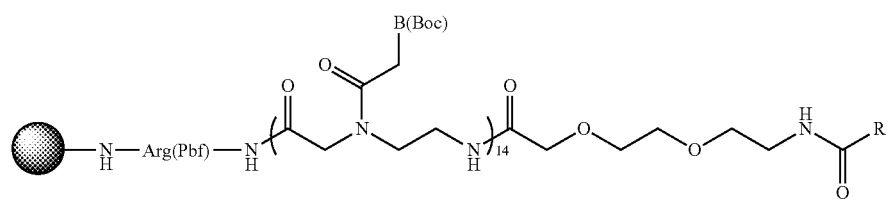

The structure of R is given in table 5 below.

Carboxylic Acid Coupling

The corresponding carboxylic acid (0.01 mmol, 5.0 equiv) was dissolved in 200 μL of NMP and HOBt (1.5 mg, 0.01 mmol, 5.0 equiv) followed by diisopropylcarbodiimide (4.7 μL, 0.03 mmol, 15.0 equiv) were added. The mixture was stirred for 15 min and then added to resin. The reaction was shaken for 8 hours at room temperature.

The structure of R is given in the table below.

Alcohol/Amine Coupling Via Chloroformate Activation 4-nitrophenyl chloroformate (3.2 mg, 0.016 mmol, 8.0 equiv) and 2,6 lutidine (3.8 μL, 0.032 mmol, 16.0 equiv) were dissolved in 200 μL of 1,2-dichloroethane (solution A). 4-DMAP (2 mg, 0.016 mmol, 8 equiv) was dissolved in 28 μL of 1,2-dichloroethane (solution B). Solution A, followed by solution B were added to resin and the reaction was shaken for 16 h at room temperature. The resin was subsequently washed with 1,2-dichloroethane, and the activation procedure was repeated a second time. Finally, the resin was washed with DMF and $CH_2Cl_2$. The alcohol or amine (0.07 mmol, 35.0 equiv), followed by DIPEA (23.1 μL, 0.14 mmol, 70.0 equiv—only for amine hydrochlorides) and DMAP (24.4 mg, 0.20 mmol, 100.0 equiv) were dissolved in 280 μL 1,2-dichloroethane. Then, the solution was added to resin IV, and the reaction was shaken for 16 h at 50° C. Finally, the resin was washed with DMF and $CH_2Cl_2$.

Alcohol/Amine Coupling Via Diglycolic Anhydride

Diglycolic anhydride (2.3 mg, 0.02 mmol, 10.0 equiv) and 2,6 lutidine (4.7 μL, 0.04 mmol, 20.0 equiv) were dissolved in 200 μL NMP. The solution was added to resin and the reaction was shaken for 16 h at room temperature. Finally, the resin was washed with DMF and $CH_2Cl_2$. BOP (7.1 mg, 0.016 mmol, 8.0 equiv), HOBt (2.5 mg, 0.016 mmol, 8.0 equiv) and DIPEA (4.2 μL, 0.024 mmol, 12.0 equiv) were dissolved in 100 μL NMP. The solution was added to the resin and the reaction was shaken for 20 min. An amine or alcohol (0.02 mmol, 10.0 eq), followed by DIPEA (6.7 μL, 0.04 mmol, 20.0 equiv—only for amine hydrochlorides) and DMAP (4.9 mg, 0.040 mmol, 20 equiv) were dissolved in 100 μL NMP. The solution was subsequently added to the resin, after removing the activation solution, and the reaction was shaken for 16 h at 35° C. Finally, the resin was washed with DMF and $CH_2Cl_2$.

VI

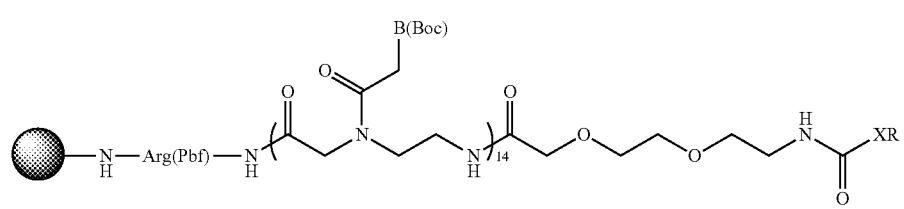

X = O, NH or NR'

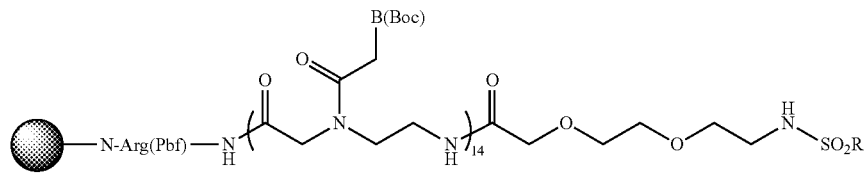

10

The structure of R is given in the table below.

Sulfonyl Chlorines Coupling

The resin were treated with a solution of the corresponding sulfonyl chlorine (0.02 mmol, 10.0 equiv) and diisopropylamine (0.04 mmol, 20.0 equiv) in 200 μL of NMP. The reaction was shaken for 8 hours at room temperature. Finally, the resin was washed with DMF and $CH_2Cl_2$.

TABLE 5

Different structures as element of diversity

| Entry | PNA Sequence | Structure |
|---|---|---|
| 1 | GCCG T*GG GTG* AGGC | $HO_2C$—〈benzene〉—$BF_3K$ |
| 2 | GCCG C*CG GTG* AGGC | NC-pyridine-$CO_2H$ |
| 3 | GCCG G*CA GTG* AGGC | methylenedioxyphenyl-CH=CH-$CO_2H$ |
| 4 | GCCG C*GA GTG* AGGC | diphenyl pyrazolidinedione with butyl and $CO_2H$ ester chain |
| 5 | GCCG G*GC GTG* AGGC | fluoroquinolone with Me, F, $CO_2H$ |
| 6 | GCCG T*GG GCA* AGGC | HO-phenyl-CH(OH)-CH(Me)-$NH_2$ |

TABLE 5-continued
Different structures as element of diversity
| Entry | PNA Sequence | Structure |
|---|---|---|
| 7 | GCCG C*CG GCA* AGGC | 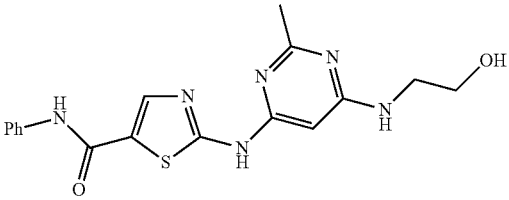 [SMILES: Cc1nc(NCCO)cc(Nc2ncc(C(=O)Nc3ccccc3)s2)n1] |
| 8 | GCCG G*CA GCA* AGGC | 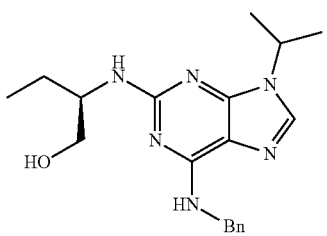 [SMILES: CC[C@H](CO)Nc1nc(NCc2ccccc2)c2ncn(C(C)C)c2n1] |
| 9 | GCCG C*GA GCA* AGGC | 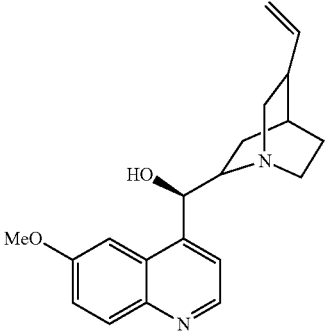 [SMILES: C=CC1CN2CCC1CC2[C@H](O)c1ccnc2ccc(OC)cc12] |
| 10 | GCCG G*GC GCA* AGGC | 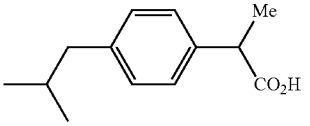 |
| 11 | GCCG T*GG ACG* AGGC | 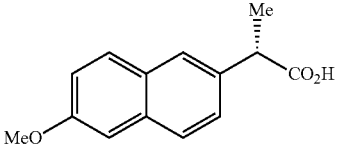 [SMILES: COc1ccc2cc([C@H](C)C(=O)O)ccc2c1] |
| 12 | GCCG C*CG ACG* AGGC | 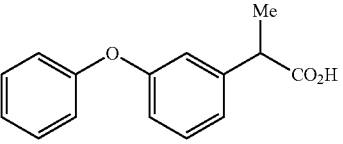 [SMILES: CC(C(=O)O)c1cccc(Oc2ccccc2)c1] |
| 13 | GCCG G*CA ACG* AGGC | 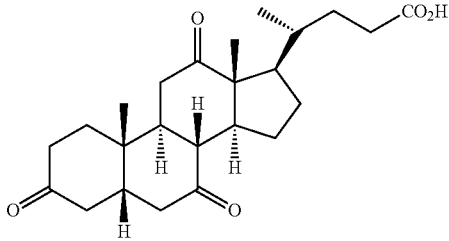 |

TABLE 5-continued
Different structures as element of diversity
| Entry | PNA Sequence | Structure |
|---|---|---|
| 14 | GCCG C*GA ACG* AGGC | 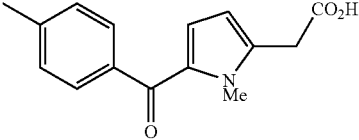 [SMILES: Cc1ccc(C(=O)c2ccc(CC(=O)O)n2C)cc1] |
| 15 | GCCG G*GC ACG* AGGC | 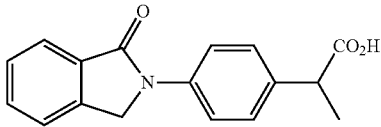 [SMILES: CC(C(=O)O)c1ccc(N2Cc3ccccc3C2=O)cc1] |
| 16 | GCCG T*GG CGA* AGGC | 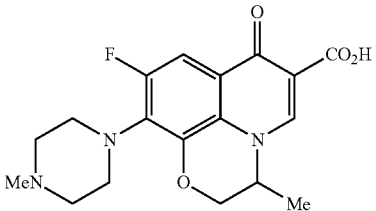 [SMILES: CC1COc2c(N3CCN(C)CC3)c(F)cc3c(=O)c(C(=O)O)cn1c23] |
| 17 | GCCG C*CG CGA* AGGC | 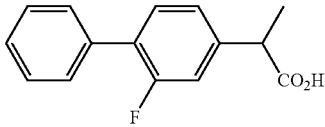 [SMILES: CC(C(=O)O)c1ccc(-c2ccccc2)c(F)c1] |
| 18 | GCCG G*CA CGA* AGGC | 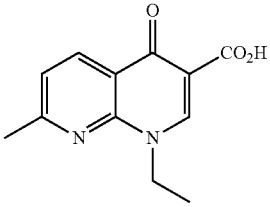 [SMILES: CCn1cc(C(=O)O)c(=O)c2ccc(C)nc21] |
| 19 | GCCG C*GA CGA* AGGC | 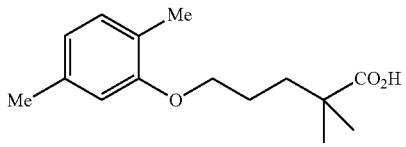 [SMILES: Cc1ccc(C)c(OCCCC(C)(C)C(=O)O)c1] |
| 20 | GCCG G*GC CGA* AGGC | 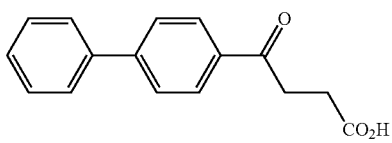 |
| 21 | GCCG T*GG AGC* AGGC | 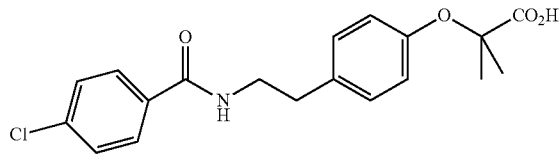 [SMILES: CC(C)(Oc1ccc(CCNC(=O)c2ccc(Cl)cc2)cc1)C(=O)O] |

TABLE 5-continued
Different structures as element of diversity
| Entry | PNA Sequence | Structure |
|---|---|---|
| 22 | GCCG C*CG AGC* AGGC | 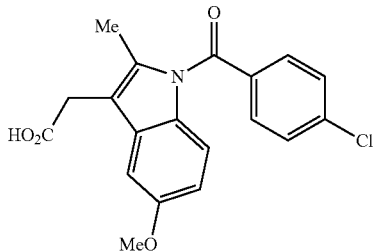 [SMILES: COc1ccc2c(c1)c(CC(=O)O)c(C)n2C(=O)c1ccc(Cl)cc1] |
| 23 | GCCG G*CA AGC* AGGC | 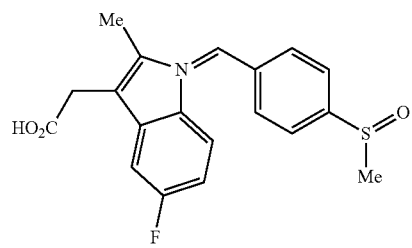 |
| 24 | GCCG C*GA AGC* AGGC | 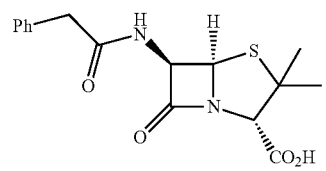 [SMILES: CC1(C)S[C@@H]2[C@H](NC(=O)Cc3ccccc3)C(=O)N2[C@H]1C(=O)O] |
| 25 | GCCG G*GC AGC* AGGC | 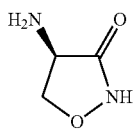 |
| 26 | GGAA T*GG GTG* AGGC | 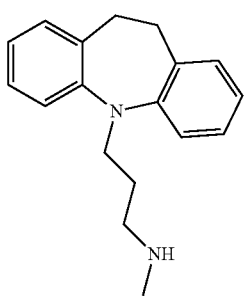 [SMILES: CNCCCN1c2ccccc2CCc2ccccc21] |
| 27 | GGAA C*CG GTG* AGGC | 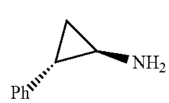 |
| 28 | GGAA G*CA GTG* AGGC | 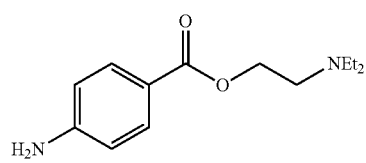 |

TABLE 5-continued

Different structures as element of diversity

| Entry | PNA Sequence | Structure |
|---|---|---|
| 29 | GGAA C*GA GTG* AGGC | 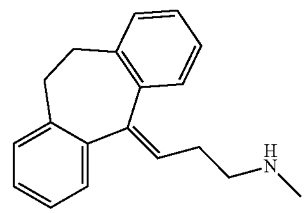 [SMILES: CNCCC=C1c2ccccc2CCc2ccccc21] |
| 30 | GGAA G*GC GTG* AGGC | 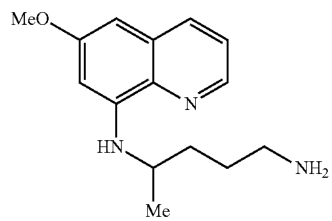 [SMILES: COc1cc(NC(C)CCCN)c2ncccc2c1] |
| 31 | GGAA T*GG GCA* AGGC | 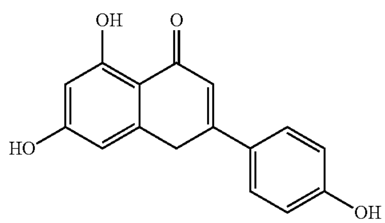 [SMILES: O=C1C=C(c2ccc(O)cc2)Cc2cc(O)cc(O)c21] |
| 32 | GGAA T*CG GCA* AGGC | 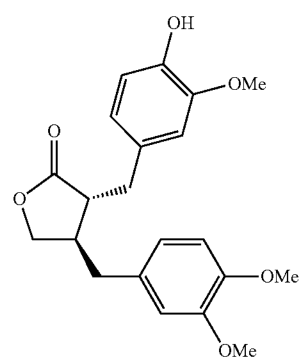 [SMILES: COc1cc(C[C@H]2C(=O)OC[C@@H]2Cc2ccc(OC)c(OC)c2)ccc1O] |
| 33 | GGAA G*CA GCA* AGGC | 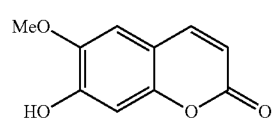 [SMILES: COc1cc2ccc(=O)oc2cc1O] |
| 34 | GGAA C*GA GCA* AGGC | 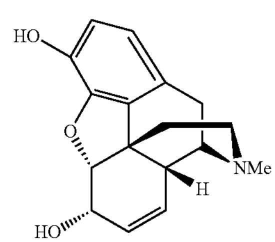 |
| 35 | GGAA G*GC GCA* AGGC | 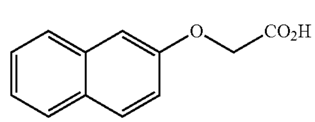 [SMILES: O=C(O)COc1ccc2ccccc2c1] |

TABLE 5-continued

Different structures as element of diversity

| Entry | PNA Sequence | Structure |
|---|---|---|
| 36 | GGAA T*GG ACG* AGGC | (sulfanilamide-acetyl derivative: 4-aminophenyl-SO2-NH-C(O)-CH3) |
| 37 | GGAA C*CG ACG* AGGC | (aminoglutethimide: 3-ethyl-3-(4-aminophenyl)piperidine-2,6-dione) |
| 38 | GGAA G*CA ACG* AGGC | (3-amino-1H-1,2,4-triazole) |
| 39 | GGAA C*GA ACG* AGGC | (butyl 4-aminobenzoate) |
| 40 | GGAA G*GC ACG* AGGC | (4-hydroxy-α-(aminomethyl)benzyl alcohol) |
| 41 | GGAA T*GG CGA* AGGC | (tropinone derivative with OH) |
| 42 | GGAA C*CG CGA* AGGC | (serotonin: 5-hydroxytryptamine) |
| 43 | GGAA G*CA CGA* AGGC | (carvedilol) |

TABLE 5-continued

Different structures as element of diversity

| Entry | PNA Sequence |
|---|---|
| 44 | GGAA C*GA CGA* AGGC |
| 45 | GGAA G*GC CGA* AGGC |
| 46 | GGAA T*GG AGC* AGGC |
| 47 | GGAA C*CG AGC* AGGC |
| 48 | GGAA G*CA AGC* AGGC |
| 49 | GGAA C*GA AGC* AGGC |
| 50 | GGAA G*GC AGC* AGGC |
| 51 | CGGC T*GG GTG* AGGC |

TABLE 5-continued
Different structures as element of diversity
| Entry | PNA Sequence | Structure |
|---|---|---|
| 52 | CGGC C*CG GTG* AGGC | 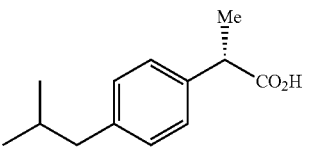 |
| 53 | CGGC G*CA GTG* AGGC | 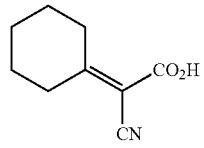 [SMILES: N#CC(C(=O)O)=C1CCCCC1] |
| 54 | CGGC C*GA GTG* AGGC | 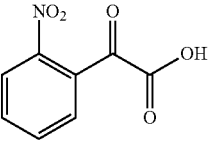 [SMILES: O=C(O)C(=O)c1ccccc1[N+](=O)[O-]] |
| 55 | CGGC G*GC GTG* AGGC | 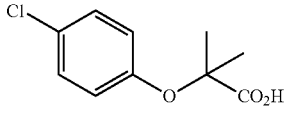 |
| 56 | CGGC T*GG GCA* AGGC | 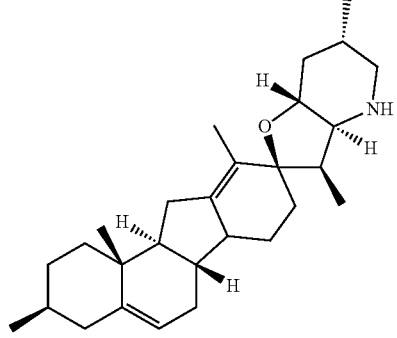 [SMILES: CC1=C2C[C@H]3[C@@H](CC=C4C[C@@H](C)CC[C@@]43C)C2CC[C@]12O[C@@H]1C[C@H](C)CN[C@H]1[C@H]2C] |
| 57 | CGGC C*CG GCA* AGGC | 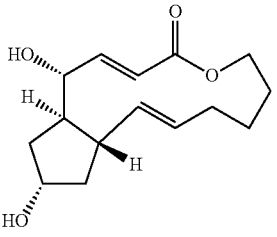 [SMILES: O=C1/C=C/[C@@H](O)[C@@H]2C[C@@H](O)C[C@H]2/C=C/CCCCO1] |
| 58 | CGGC G*CA GCA* AGGC | 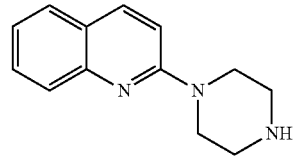 [SMILES: c1ccc2nc(N3CCNCC3)ccc2c1] |

TABLE 5-continued

Different structures as element of diversity

| Entry | PNA Sequence | Structure |
|---|---|---|
| 59 | CGGC C*GA GCA* AGGC | (1,4-diazepan-1-ylsulfonyl)isoquinoline |
| 60 | CGGC G*GC GCA* AGGC | 2',4'-difluoro-4-hydroxy-[1,1'-biphenyl]-3-carboxylic acid |
| 61 | CGGC T*GG ACG* AGGC | (Z)-3-(naphthalen-1-yl)acrylic acid |
| 62 | CGGC C*CG ACG* AGGC | (E)-3-(pyridin-3-yl)acrylic acid |
| 63 | CGGC G*CA ACG* AGGC | 2-(2-(4-((4-chlorophenyl)(phenyl)methyl)piperazin-1-yl)ethoxy)acetic acid |
| 64 | CGGC C*GA ACG* AGGC | (E)-3-(4-(dimethylamino)phenyl)acrylic acid |
| 65 | CGGC G*GC ACG* AGGC | 2-cyano-7-(2,2-dimethylpropyl)-5-(hydroxymethyl)-7H-pyrrolo[2,3-d]pyrimidine |
| 66 | CGGC T*GG CGA* AGGC | 2-oxo-2-phenylacetic acid |

TABLE 5-continued

Different structures as element of diversity

| Entry | PNA Sequence | Structure |
|---|---|---|
| 67 | CGGC C*CG CGA* AGGC | α-methyl cinnamic acid (Ph-CH=C(Me)-CO₂H) |
| 68 | CGGC G*CA CGA* AGGC | Me₂N-CH₂-CH=CH-CO₂H |
| 69 | CGGC C*GA CGA* AGGC | 4-AcHN-C₆H₄-CH=CH-CO₂H |
| 70 | CGGC G*GC CGA* AGGC | (CH₃)₂C=CH-CO₂H |
| 71 | CGGC T*GG AGC* AGGC | 3-(HO₂C)-5-(BF₃K)-C₆H₄ (benzene with BF₃K and HO₂C) |
| 72 | CGGC C*CG AGC* AGGC | 4-((HO)₂B)-C₆H₄-CH=CH-CO₂H |
| 73 | CGGC G*CA AGC* AGGC | Me-C(=O)-C(=O)-OH |
| 74 | CGGC C*GA AGC* AGGC | Pr-C(=O)-C(=O)-OH |
| 75 | CGGC G*GC AGC* AGGC | iPr-C(=O)-C(=O)-OH |
| 76 | AAGG T*GG GTG* AGGC | 2-thienyl-CH=CH-CO₂H |
| 77 | AAGG C*CG GTG* AGGC | Ph-CH=CH-CO₂H |
| 78 | AAGG G*CA GTG* AGGC | 2-Br-C₆H₄-CH=CH-CO₂H |
| 79 | AAGG C*GA GTG* AGGC | Ph-C(=O)-CH=CH-CO₂H |

TABLE 5-continued

Different structures as element of diversity

| Entry | PNA Sequence | Structure |
|---|---|---|
| 80 | AAGG G*GC GTG* AGGC | phenyl-C(CN)=CH-CO₂H (α-cyanocinnamic acid) |
| 81 | AAGG T*GG GCA* AGGC | tetramethyltetrahydronaphthalene with vinyl linked to 4-(CO₂H)phenyl |
| 82 | AAGG C*CG GCA* AGGC | N-methyl tropane-3-ol (tropine) |
| 83 | AAGG G*CA GCA* AGGC | abietic acid (tricyclic diterpene with isopropyl and HO₂C, methyl) |
| 84 | AAGG C*GA GCA* AGGC | 2-phenylquinoline-4-carboxylic acid |
| 85 | AAGG G*GC GCA* AGGC | zomepirac-like: 5-(4-chlorobenzoyl)-1,4-dimethyl-1H-pyrrole-2-acetic acid |
| 86 | AAGG T*GG ACG* AGGC | HO₂C-CH₂-CN (cyanoacetic acid) |
| 87 | AAGG C*CG ACG* AGGC | 1-cyanocyclopropanecarboxylic acid |
| 88 | AAGG G*CA ACG* AGGC | ethacrynic acid (2,3-dichloro-4-(2-methylenebutanoyl)phenoxyacetic acid) |

TABLE 5-continued

Different structures as element of diversity

| Entry | PNA Sequence | Structure |
|---|---|---|
| 89 | AAGG C*GA ACG* AGGC | 2-acetoxybenzoic acid (aspirin) |
| 90 | AAGG G*GC ACG* AGGC | 2,6-dimethoxybenzamido penicillin (methicillin), CO$_2$Na salt |
| 91 | AAGG T*GG CGA* AGGC | 4-hydroxyacetanilide (paracetamol) |
| 92 | AAGG C*CG CGA* AGGC | 1-(2,6-dimethylphenoxy)propan-2-amine (mexiletine) |
| 93 | AAGG G*CA CGA* AGGC | 1-adamantanamine (amantadine) |
| 94 | AAGG C*GA CGA* AGGC | (1S)-(+)-camphor-10-sulfonyl chloride |
| 95 | AAGG G*GC CGA* AGGC | naphthalene-2-sulfonyl chloride |
| 96 | AAGG T*GG AGC* AGGC | aristolochic acid |
| 97 | AAGG C*CG AGC* AGGC | ketorolac |

TABLE 5-continued

Different structures as element of diversity

| Entry | PNA Sequence | Structure |
|---|---|---|
| 98 | AAGG G*CA AGC* AGGC | 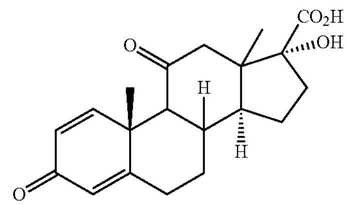 |
| 99 | AAGG C*GA AGC* AGGC | 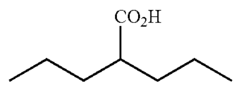 |
| 100 | AAGG G*GC AGC* AGGC | 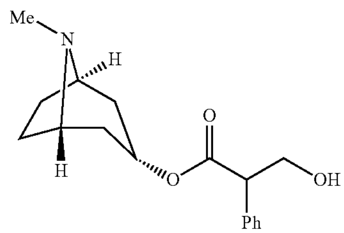 [SMILES: CN1[C@@H]2CC[C@H]1C[C@@H](OC(=O)C(CO)c1ccccc1)C2] |
| 101 | GAAC T*GG GTG* AGGC | 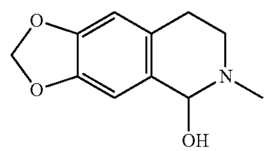 |
| 102 | GAAC C*CG GTG* AGGC | 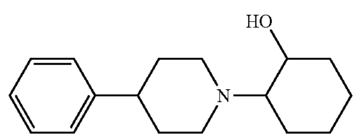 [SMILES: OC1CCCCC1N1CCC(c2ccccc2)CC1] |
| 103 | GAAC G*CA GTG* AGGC | 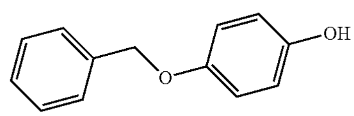 [SMILES: Oc1ccc(OCc2ccccc2)cc1] |
| 104 | GAAC C*GA GTG* AGGC | 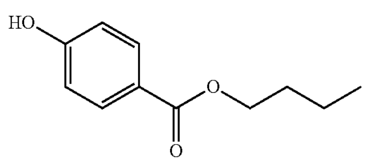 |
| 105 | GAAC G*GC GTG* AGGC | 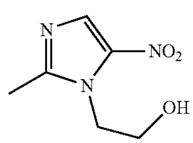 |
| 106 | GAAC T*GG GCA* AGGC | 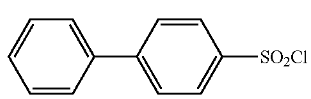 [SMILES: O=S(=O)(Cl)c1ccc(-c2ccccc2)cc1] |
| 107 | GAAC C*CG GCA* AGGC | 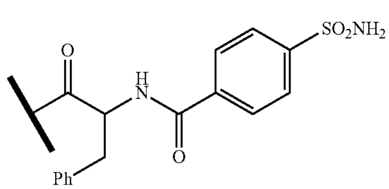 |

TABLE 5-continued
Different structures as element of diversity
| Entry | PNA Sequence | Structure |
|---|---|---|
| 108 | GAAC G*CA GCA* AGGC | 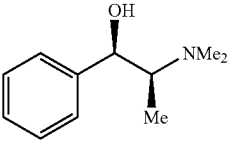 [SMILES: C[C@@H]([C@H](O)c1ccccc1)N(C)C] |
| 109 | GAAC C*GA GCA* AGGC | 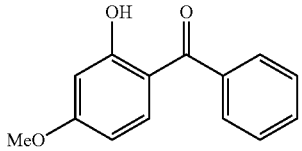 [SMILES: COc1ccc(C(=O)c2ccccc2)c(O)c1] |
| 110 | GAAC G*GC GCA* AGGC | 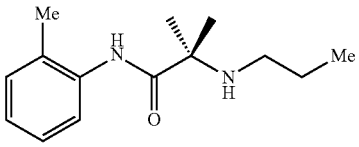 |
| 111 | GAAC T*GG ACG* AGGC | 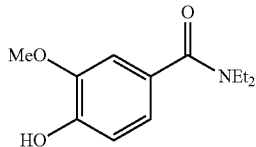 |
| 112 | GAAC C*CG ACG* AGGC | 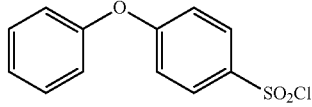 [SMILES: O=S(=O)(Cl)c1ccc(Oc2ccccc2)cc1] |
| 113 | GAAC G*CA ACG* AGGC | Me$_2$N—SO$_2$Cl |
| 114 | GAAC C*GA ACG* AGGC | 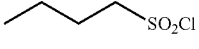 |
| 115 | GAAC G*GC ACG* AGGC | 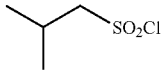 |
| 116 | GAAC T*GG CGA* AGGC | 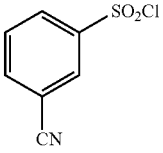 |
| 117 | GAAC C*CG CGA* AGGC | 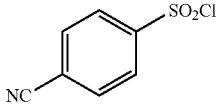 [SMILES: N#Cc1ccc(S(=O)(=O)Cl)cc1] |
| 118 | GAAC G*CA CGA* AGGC | 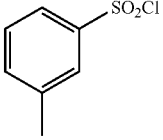 |
| 119 | GAAC C*GA CGA* AGGC | 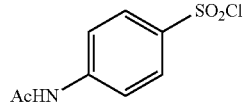 [SMILES: CC(=O)Nc1ccc(S(=O)(=O)Cl)cc1] |

TABLE 5-continued

Different structures as element of diversity

| Entry | PNA Sequence | Structure |
|---|---|---|
| 120 | GAAC G*GC CGA* AGGC | 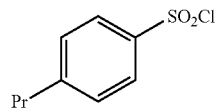 |
| 121 | GAAC T*GG AGC* AGGC | 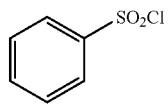 |
| 122 | GAAC C*CG AGC* AGGC | 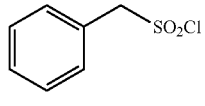 [SMILES: O=S(=O)(Cl)Cc1ccccc1] |
| 123 | GAAC G*CA AGC* AGGC | 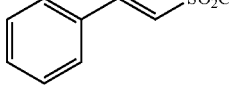 |
| 124 | GAAC C*GA AGC* AGGC | 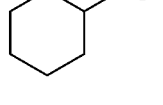 |
| 125 | GAAC G*GC AGC* AGGC | 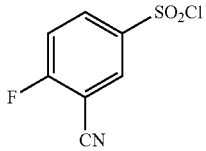 [SMILES: N#Cc1cc(S(=O)(=O)Cl)ccc1F] |

*means a modified PNA (GPNA) according to Imaging of mRNA in Live Cells Using Nucleic-Acid Templated Reduction of Azidorhodamine Probes, Z. Pianowski, K. Gorska, L. Oswald, C. A. Merten, N. Winssinger, *J. Am. Chem. Soc.*, 2009, 6492-6497.

EXAMPLE 6

Figure 5:
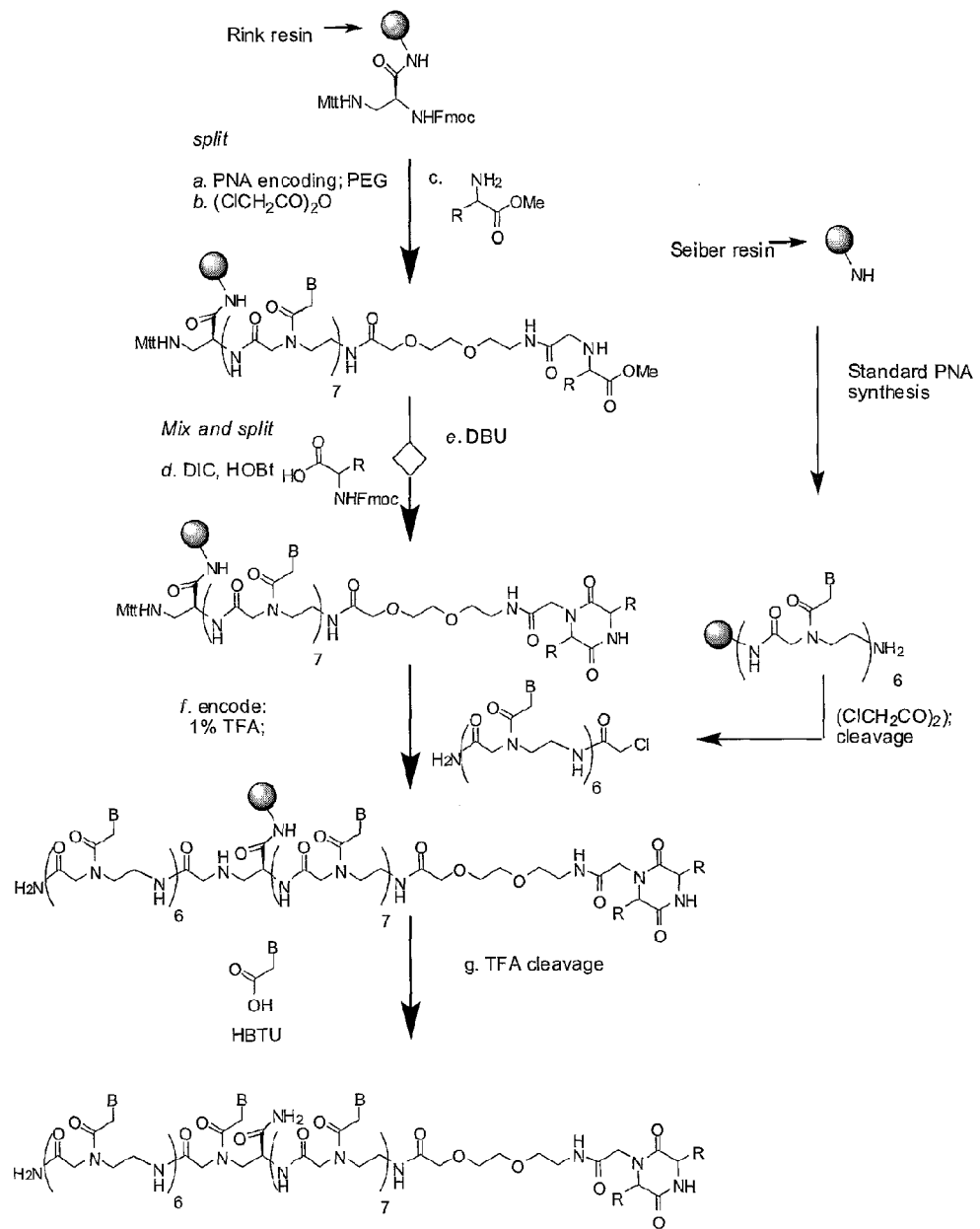
FIG. 5 shows the synthesis of a PNA-encoded library where the molecule is appended at the N-terminus according to example 6.

Split and Mix Synthesis of PNA Libraries Appended at N-Terminus of PNA 6.1. Synthesis of PNA Libraries Appended at N-Terminus of PNA Such synthesis is illustrated in FIG. 5 wherein an example of a library of diketopiperizines is proposed as it is a well documented pharmacophore. However, this strategy is also applicable to libraries shown in the previous scheme.

Starting with the Fmoc (Mtt) protected amino analogue of serine which is linked to a Rink resin, standard PNA synthesis can be carried out following the deprotection of the Fmoc with the codon for the first element of diversity. The resin is then be mixed and split and the second element of diversity is introduced. The Mtt is then removed and the amino group is reacted with a PNA oliogomer encoding the second element of diversity earring a chloroacetamide at the N-terminus. Such oligomers is prepared on a Sieber resin which allows the cleavage of the oligomers with all the nucleobases protected (Boc-protected nucleobases are compatible with 1% TFA treatment required for Sieber resin cleavage). The product of the coupling is acylated with the appropriate nucleobase to complete the PNA.

6.2. Split and Mix Synthesis of PNA Libraries Appended at N-Terminus of PNA

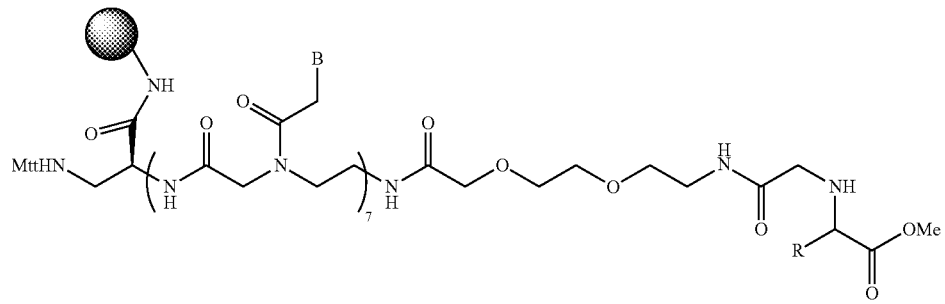

R represents the side chain of any natural of non-natural amino acid.

Rink resin (NovaPEG) was loaded with the Fmoc (Mtt) protected amino analogue of serine (commercially available) using the same procedure as described for Lys (procedure 5) distributed in 25 columns and the first PNA codon was introduced using (procedure 10) followed by a PEG spacer (procedure 6) and chloroacetylation (procedure 16). The chloroacetamide was displaced with aminoacids methyl esters (5 equiv) in the presence of base (EtiPr$_2$N, 10 equiv) in DMF at 50° C. for 12 h.

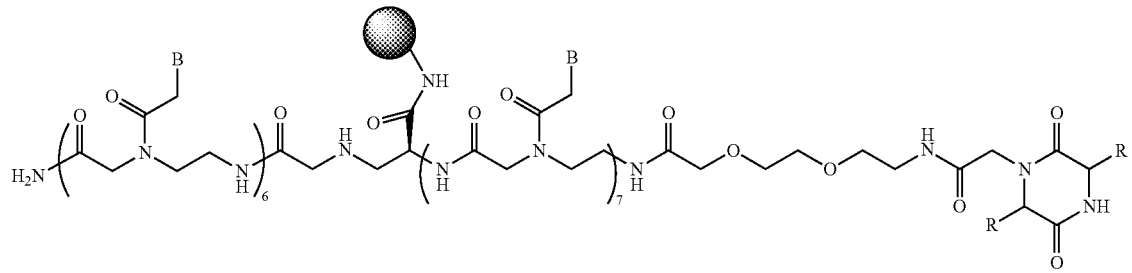

R represents the same or different side chain of any natural of non-natural amino acid.

The resin was split and mixed and redistributed in 20 columns to be coupled to an Fmoc protected amino acid (5 equiv, HATU 5 equiv, EtiPr$_2$N 5 equiv) in DMF at rt for 12 h. The resin was than treated with DBU (2 equiv) in DMF at rt for 3 hours to promote the Fmoc deprotection and cyclization. The MTT was removed (procedure 9). The identity of the amino acid was then encoded by the addition of a PNA codon capped with a chloroacetamide (procedure 16) previously synthesized (procedure 10) on a Sieber resin thus enabling the cleavage of the protected PNA fragment with the same procedure as an MTT deprotection (1:1 HFIP:DCE). The solution of the cleavage was concentrated and added to the resin (2 equiv of PNA-chloroacetamide, EtiPr$_2$N 5 equiv) as a DMF solution and the reaction was heated to 50° C. for 12 h. The resin was washed with DMF and the amine acylated with the corresponding nucleobase (5 equiv, HATU 5 equiv, EtiPr$_2$N 5 equiv—for preparation of the nucleobase, see: S. Pothukanuri, Z. Pianowski, N. Winssinger, *Eur. J. Org. Chem.*, 2008, 18, 3141-48). The library was cleaved from the resin and the completion of every step was confirmed by MALDI analysis.

EXAMPLE 7

Procedure for the Selection of the Fittest Combination in a PNA-DNA Hybrid Library A library of DNA containing all permutation of codons complementary to the PNA libraries flanked by 20-mer primer was obtained by split and pool synthesis from commercial supplier (Microsynth AG, Switzerland). For example, for screening hybrid library composed of two PNA-encoded libraries of 125 compounds (library A, 14mer PNA) and 500 compounds (library B, 14mer PNA) a 68mer DNA library of 62 500 (125×500) combination was used.

The self assembled library was prepared by mixing the PNA library A (N-terminus PNA) and B (C-terminus PNA) with the DNA library as well as sequences complementary to the primers on the DNA library (P5' block 5'-ACGAGAG-GCTCACAACAGGC-3' (SEQ ID NO: 1) and P3' block, 5'-GGATAGACAATAACGACGAC-3' (SEQ ID NO: 2)). All the component were mixed at equal molar ratio to obtain a final concentration 600 nM in 50 mM, Tris —SO$_4$ buffer, pH 8.7 or alternatively PBS buffer, NaCl, 0.2 M, in a final volume of 100 µL. The mixture was heat denatured (10 min at 95° C.) and the hybridization mix was cool down to room temperature for one hour.

Carbonic anhydrase (CA) (Sigma®) was dissolved in PBS at 2 mg/ml and immobilized on carboxylic acid activated magnetic beads (Dynal® Invitrogen™) following the manufacturer recommendations. 10 µg of immobilized CA were used at each selection round.

The DNA/PNA hybrids solution (10 µL) was incubated with the target immobilized protein slurry (10 µL) for 30 min at RT with gentle agitation. After incubation the tubes were the selection took place were placed on a magnetic stand for 2 minutes and the supernatant containing the non bound molecules was pipetted off and discarded. The retained candidates were washed 10 times with PBS-Tween 20, 0.1% (PBS-T) 100 µL, to eliminate PNA/DNA hybrids non specifically interacting with the target. After 10 washes, The CA functionalized magnetic beads were resuspended on 50 µL of distilled water and heated at 94° C. for 10 min. Then the tubes were placed on a magnetic stand and the supernatant containing the selected candidates was recovered in a new tube, diluted 100 times and 1 µL of this dilution was used as template for PCR amplification. The same procedure was carried out in parallel with BSA functionalized magnetic beads to identify specific selection corresponding to CA by comparison of the selected compounds.

PCR DNA Amplification and ssDNA Preparation

DNA/PNA hybrids recovered after selection by heat elution were used as templates on PCR amplification under the following conditions. PCR reactions containing 2 µM primer P3' Cy3-5'-GGATAGACAATAACGACGAC-3' (SEQ ID NO: 4), 2 µM primer P5' Biot-5'-GCCTGTTGTGAGC-CTCTCGT-3' (SEQ ID NO: 3), 0.2 units of AmpliTaq Gold® (Applied Biosystems™), 1.5 mM MgCl$_2$, AmpliTaq Gold® Buffer II, were amplified as follows: one first incubation at 95° C. for 10 min, 95° C. during 1 min, 52° C. for 30 s, 68° C. for 30 s (25 cycles) and a final elongation 10 min at 72° C.

The PCR reactions were analyzed on 3.5% agarose electrophoresis to confirm the amplification of a specific 68 nucleotides product, stained with ethidium bromide and visualized by UV transillumination.

100 µl of PCR reaction from each round of selection were purified using Quiaquick PCR purification kit (Qiagen®). The purified PCR product was immobilized on Dynal® Streptavidine magnetic beads, and single strand DNA was prepared following a known protocol (Martin Beaulieu, Garry P. Larson, Louis Geller, Steven D. Flanagan and Theodore G. Krontiris, Nucleic Acids Research, 2001, Vol. 29, No. 5 1114-1124).

The Cy3 labeled DNA strand (ss-FDNA) was conserved at −20° C. until hybridization on microarray slides while the immobilized biotinylated strand (template strand) was rehybridized with the PNA libraries A and B (600 nM) during 30 min at 50° C. The non hybridized PNA molecules were washes out of the magnetic beads by five successive washes with 100 µl PBS-T at room temperature. The new recruited PNA/DNA hybrids were eluted from the magnetic beads by heating the beads at 95° C. (10 µl) for ten minutes on PBS buffer, 5 mM biotin. The eluted DNA/PNA hybrids were engaged in further rounds of selection by using the recover solution to incubate with the immobilized target.

The Cy3 labeled DNA strands corresponding to several rounds of selection were hybridized to custom array containing the complementary sequences as previously described (H. D. Urbina, F. Debaene, B. Jost, C. Bole-Feysot, P. Kuzmic, J. L. Harris, N. Winssinger *ChemBioChem*, 2006, 7, 1790-1797).

The covalent adducts from selected fragments were resynthesized on each arm of a bifunctional linker (such as FmocLys(Mtt)OH) by the same protocol as used in the original library synthesis. Different distances between the ligands were achieved using different bifunctional linker. The products obtain following cleavage from the resin were tested for their activity and affinity by enzymatic assay or microcalorimetry.

For carbonic anhydrase (CA)-, bovine CA II 50 nM was incubated with variable concentrations of the selected compounds for 10 min prior to addition of 4-nitrophenyl acetate. The assay was done on Tris-SO4 50 mM, pH 8.5, and 4-nitrophenyl acetate concentration of 1 mM on 96 well plates, 200 µl reaction volume.

Auto hydrolysis of 4-nitrophenyl acetate was subtracted from the observed Vmax. Absorbance kinetics were measured with a plate reader (Molecular devices). Affinity of the selected compounds to carbonic anhydrase was also measured using a microcalorimetric ITC 200 (Microcal®). A 500 µM solution of ligand on buffer Tris-SO4, 50 mM, pH 8.5, 2% DMSO was titrated with a 25 µM solution of Carbonic anhydrase (Sigma®) on the same buffer at 25° C. The isothermal titration curves obtained were treated and fitted using Origin 7 software (OriginLab®).

EXAMPLE 8

Figure 6:
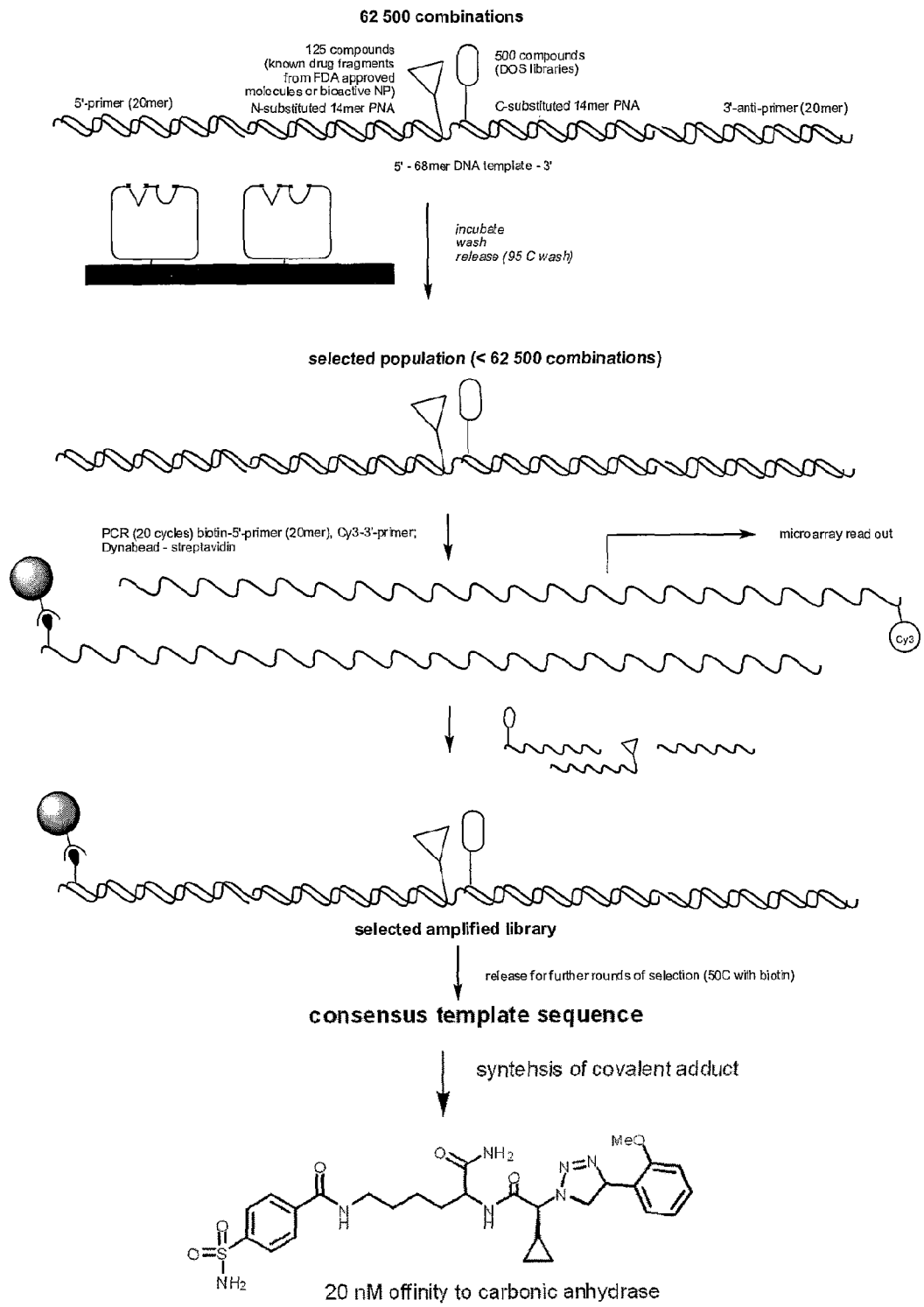
FIG. 6 illustrates the screening of a DTSAL against carbonic anhydrase and the identification of an inhibitor of carbonic anhydrase according to example 8.

Screening of a DTSAL and Obtaining of an Adduct Having High-Affinity to Carbonic Anhydrase As shown in FIG. 6, the protocol for the screening of DTSAL involves a reiteration of three steps: hybridization of the PNA-encoded libraries onto a DNA template library, passing the library over the immobilized target to retain the best binders, and amplification and capture of the selected templates. The immobilization of the target protein can be carried out on magnetic beads (such as Dynabeads) or SPR sensor chip using standard protocols. As was exemplified with carbonic anhydrase using two PNA libraries affording 62500 combinations, the 10 micrograms of target was immobilized and incubated with 50 microliters of the library at a total concentration of 100 micromolar. The target was washed five times with buffer then heated to 95 degree Celsius to recover the DNA template corresponding to the best ligand combination. The DNA template was amplified (20 cycles of PCR) with PCR primers containing a biotin (5' primer) and a fluorophore (3' primer) and the PCR product was captured on a streptavidin resin. Dissociation of the two strands afforded the fluorophore labeled strand in solution which was analyzed by hybridization to a microarray. The templating DNA strand which remained associated to the streptavidin resin was incubated with the library of PNA-encoded molecules and subsequently release by heating to 50 degree Celsius in the presence of an excess of biotin. The selected population of DNA-templated library was used for a second round of selection following the same procedure. This was reiterated two more times. Interestingly, hybridization of each round of selection showed a clear evolution towards a consensus sequence. The fittest combination was resynthesized as a covalent adduct and measured to have a 10 nM affinity to carbonic anhydrase thus validating the ability to self assemble libraries onto DNA template, screen such library in a miniaturized format and translate the results into a high affinity ligand (FIG. 6).

EXAMPLE 9

Application to the Discovery of Ligands Bridging Two Different Binding Pockets

Figure 7:
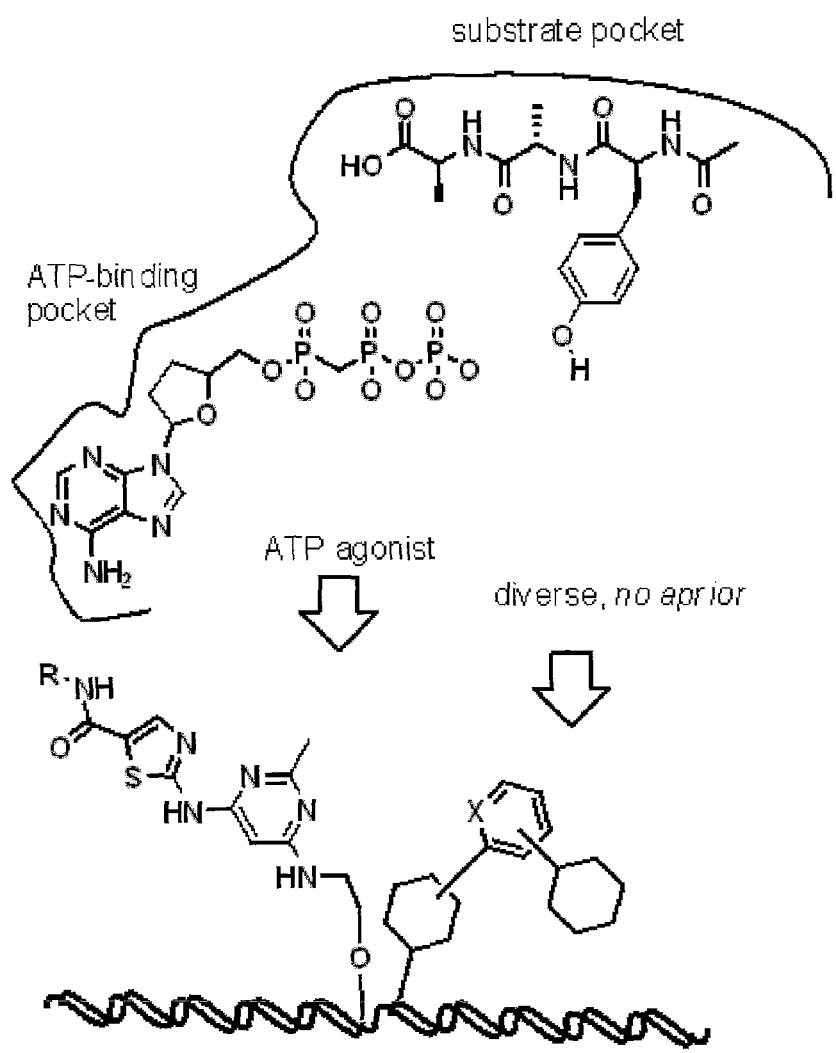
FIG. 7 represents the evolution of ligands for kinases and proteases using biased libraries. Libraries containing biasing element could further enhance ligand discovery for specific target classed.
Figure 7:
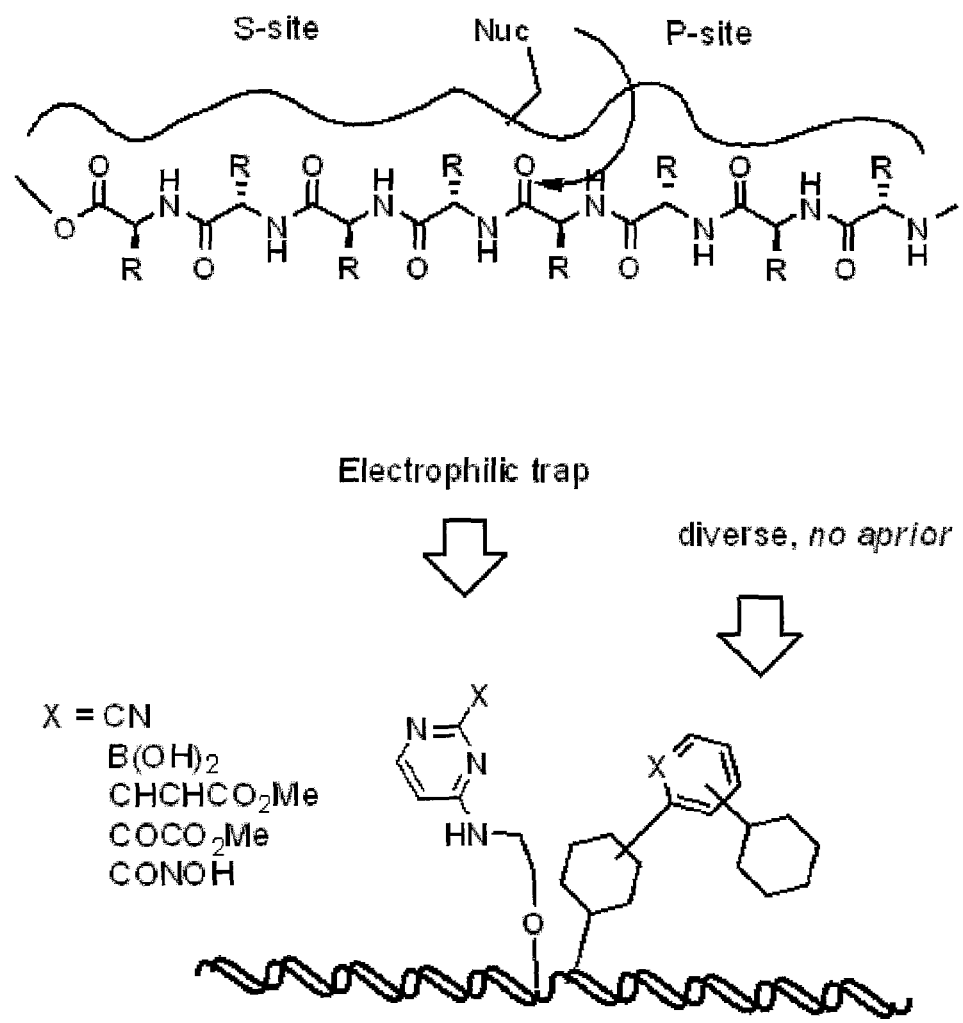

This technology readily lends itself to screen against target of interest for therapeutic intervention such as kinases and proteases. As shown in FIG. 7, libraries containing biasing element could further enhance ligand discovery for specific target classed. Receptor homo- or hetero-oligomerization is a fundamental feature of cellular recognition and signal transduction (Pin, J. P., Neubig, R., Bouvier, M., Devi, L., Filizola, M., Javitch, J. A., Lohse, M. J., Milligan, G., Palczewski, K., Parmentier, M. & Spedding, M. (2007) International Union of Basic and Clinical Pharmacology. LXVII. Recommendations for the recognition and nomenclature of G protein-coupled receptor heteromultimers Pharmacol Rev 59: 5-13; Kiessling, L. L., Gestwicki, J. E. & Strong, L. E. (2006) Synthetic multivalent ligands as probes of signal transduction Angew. Chem. Int. Ed. Engl. 45: 2348-68).

EXAMPLE 10

Protein-Carbohydrate Interaction

Protein-carbohydrate interaction often achieve high avidity by the cooperative interaction of multiple units (Lundquist, J. & Toone, E. (2002) The cluster glycoside effect Chem. Rev. 102: 555-578). An example of therapeutic significance is the interaction of the cholera toxin with cell surface carbohydrates. The toxin is a pentamer which recognizes at least five cell-surface carbohydrates. While the affinity of the toxin for the monomeric cell surface trisaccharide is in the mM range, a synthetic oligomer with an architecture matching the toxin's receptor geometry has been reported to have picomolar affinity (106 fold enhancement over the monomer) and to effectively inhibit the toxin in cellular assays (Kitov, P. I., Sadowska, J. M., Mulvey, G., Armstrong, G. D., Ling, H., Pannu, N. S., Read, R. J. & Bundle, D. R. (2000) Shiga-like toxins are neutralized by tailored multivalent carbohydrate ligands Nature 403: 669-72). While this example illustrates the importance of accessing oligomeric carbohydrate structures with controlled topology, the synthetic challenges of accessing complex architectures have hampered progress. The present invention allowing to access oligomeric carbohydrates in a combinatorial fashion with controlled topology from self assembled PNA-tagged oligosaccharides onto DNA templates is thus enabling. The potential of this method is demonstrated with different supramolecular assemblies which mimics the multiple copies of the carbohydrates (high mannose nonasaccharide, FIG. 8) shielding gp120 and known to interact in a multivalent fashion to 2G12, an antibody which broadly neutralizes HIV (Mascola, J. R., Lewis, M. G., Stiegler, G., Harris, D., Van-Cott, T. C., Hayes, D., Louder, M. K., Brown, C. R., Sapan, C. V., Frankel, S. S., Lu, Y., Robb, M. L., Katinger, H. & Birx, D. L. (1999) Protection of Macaques against pathogenic simian/human immunodeficiency virus 89.6PD by passive transfer of neutralizing antibodies J Virol 73: 4009-18; Etemad-Moghadam, B., Sun, Y., Nicholson, E. K., Karlsson, G. B., Schenten, D. & Sodroski, J. (1999) Determinants of neutralization resistance in the envelope glycoproteins of a simian-human immunodeficiency virus passaged in vivo J Virol 73: 8873-9; Crawford, J. M., Earl, P. L., Moss, B., Reimann, K. A., Wyand, M. S., Manson, K. H., Bilska, M., Zhou, J. T., Pauza, C. D., Parren, P. W., Burton, D. R., Sodroski, J. G., Letvin, N. L. & Montefiori, D. C. (1999) Characterization of primary isolate-like variants of simian-human immunodeficiency virus J Virol 73: 10199-207).

The crystal structure of 2G12 with a high-mannose sugar 1 showed that 2G12 assembled into an interlocked dimer resulting in two additional binding sites at its dimerization interface (FIG. 8) (Kunert, R., Zhu, P., Wormald Mark, R., Stanfield Robyn, L., Roux Kenneth, H., Kelly Jeffery, W., Rudd Pauline, M., Dwek Raymond, A., Katinger, H., Burton Dennis, R. & Wilson Ian, A. (2003) Antibody domain exchange is an immunological solution to carbohydrate cluster recognition Science 300: 2065-71; Calarese, D. A., Lee, H. K., Huang, C. Y., Best, M. D., Astronomo, R. D., Stanfield, R. L., Katinger, H., Burton, D. R., Wong, C. H. & Wilson, I. A. (2005) Dissection of the carbohydrate specificity of the broadly neutralizing anti-HIV-1 antibody 2G12 Proc. Natl. Acad. Sci. USA 102: 13372-7). This observation not only provided a rational for the high affinity of the antibody for its target (HIV's glycoprotein 120-gp120) by virtue of the highly cooperative binding mode but also for its selectivity for gp120 bearing high-mannose carbohydrates vs the host. Indeed, the 2G12 antibody displays appropriately spaced binding sites that match the spacing of these structures on the viral surface. Interestingly, the crystallographic information suggests that only the terminal mannoses are involved in the interaction with the antibody. While the nonasaccharide 1 has no notable affinity for 2G12, Danishefsky and coworkers have shown that a trimer of 1 displayed on a rigid scaffold binds 2G12 with moderate affinity (Krauss, I. J., Joyce, J. G., Finnefrock, A. C., Song, H. C., Dudkin, V. Y., Geng, X., Warren, J. D., Chastain, M., Shiver, J. W. & Danishefsky, S. J. (2007) Fully synthetic carbohydrate HIV antigens designed on the logic of the 2G12 antibody J Am Chem Soc 129: 11042-4) while Wang and coworkers showed that a tetramer of a mannose tetrasaccharide on a similar scaffold also bind 2G12 with micromolar affinity (Wang, J., Li, H., Zou, G. & Wang, L. (2007) Novel template-assembled oligosaccharide clusters as epitope mimics for HIV-neutralizing antibody 2G12. Design, synthesis, and antibody binding study Org. Biomol. Chem. 5: 1529-1540). The distance between the two primary binding sites in 2G12 is 30 Å (measured from pdb 1OP5 (Calarese Daniel, A., Scanlan Christopher, N., Zwick Michael, B., Deechongkit, S., Mimura, Y., Kunert, R., Zhu, P., Wormald Mark, R., Stanfield Robyn, L., Roux Kenneth, H., Kelly Jeffery, W., Rudd Pauline, M., Dwek Raymond, A., Katinger, H., Burton Dennis, R. & Wilson Ian, A. (2003) Antibody domain exchange is an immunological solution to carbohydrate cluster recognition Science 300: 2065-71)) and while some level of cooperativity has been achieved with previously reported oligomers, a more systematic investigation of optimal spacing geometry amongst the ligands to maximize the cooperativity have not been reported. In fact Danishefsky have shown that the oligomer conjugated to an immunogenic protein is able to elicit an antibody response which binds the oligomer of 1 but fails to neutralize HIV suggesting that it is not an optimal mimic of gp120's epitope. (Joyce, J. G., Krauss, I. J., Song, H. C., Opalka, D. W., Grimm, K. M., Nahas, D. D., Esser, M. T., Hrin, R., Feng, M., Dudkin, V. Y., Chastain, M., Shiver, J. W. & Danishefsky, S. J. (2008) An oligosaccharide-based HIV-1 2G12 mimotope vaccine induces carbohydrate-specific antibodies that fail to neutralize HIV-1 virions Proc Natl Acad Sci USA 105: 15684-9). Dendrons of 1 have been shown to also bind 2g12 cooperatively (Wang, S. K., Liang, P. H., Astronomo, R. D., Hsu, T. L., Hsieh, S. L., Burton, D. R. & Wong, C. H. (2008) Targeting the carbohydrates on HIV-1: Interaction of oligomannose dendrons with human monoclonal antibody 2G12 and DC-SIGN Proc. Natl. Acad. Sci. USA 105: 3690-5).

While DNA-saccharide conjugates have been reported, only monosaccharide-DNA conjugates have been reported thus far for microarraying (Chevolot, Y., Bouillon, C., Vidal, S., Morvan, F., Meyer, A., Cloarec, J. P., Jochum, A., Praly, J. P., Vasseur, J. J. & Souteyrand, E. (2007) DNA-based carbohydrate biochips: a platform for surface glyco-engineering Angew. Chem. Int. Ed. Engl. 46: 2398-402) and to study lectin interactions (Matsuura, K., Hibino, M., Yamada, Y. & Kobayashi, K. (2001) Construction of glyco-clusters by self-organization of site-specifically glycosylated oligonucleotides and their cooperative amplification of lectin-recognition J Am Chem Soc 123: 357-8; Matsuura, K., Hibino, M., Ikeda, T., Yamada, Y. & Kobayashi, K. (2004) Self-organized glycoclusters along DNA: Effect of the spatial arrangement of galactoside residues on cooperative lectin recognition Chem. Eur. J. 10: 352-359), whereas larger oligosaccharides with more complex branching patterns have never been reported.

As shown in FIG. 9, carbohydrates can be efficiently coupled to polymer-bound PNAs at the C-terminus or the N-terminus using a thiol coupling (thiolactol or carbohydrates bearing a thioalkyl group at the anomeric position) to a chloroacetamide with a mild base such as Hunigs' base or DBU. For the purpose at hand, a 10mer PNA was deemed appropriate as it would provide Tm>50° C. and would present adjacent ligand on the same face of the helix. Thus 10mer PNA 2 obtained by standard Fmoc chemistry bearing a short PEG spacer (10 Å) at the N-terminus was coupled to chloroacetyl chloride and reacted with commercially available tetracetyl glucothiolactone I in the presence of Hünig's base. Analysis of the cleavage product by LC/MS and MALDI indicated complete conversion and showed a single peak for product 3. The acetyl group on the glucose were removed by treatment with ammonia in MeOH which was found to be equally efficient prior to or after TFA cleavage from the resin. The same procedure was applied for the coupling of unprotected disaccharide II (FIG. 9) to afford after cleavage conjugate 4. To our gratification, no trace of glycosidic cleavage was observed upon acidic treatment. Saccharides labeled with a thioalkyl group at the anomeric position (48) could also be efficiently coupled to the chloroacetamide PNA but using DBU rather than Hünig's base thus affording conjugate 5 after cleavage. A similar strategy was used to install two units of the carbohydrate starting from PNA 2 by treatment of the chloroacetamide product with ethylene diamine. The resulting PNA diamine conjugate was then treated with chloracetyl chloride followed by thiosaccharide to obtain after cleavage product 6 bearing two copies of the carbohydrate. Assuming a trans or anti conformation for all bonds, the distance between the anomeric group of the two carbohydrate unit is 11.5 Å. Conversely, PNA 2 can be coupled to an orthogonally protected lysine (Fmoc, Mtt). Deprotection of both Fmoc and Mtt (Pothukanuri, S., Pianowski, Z. & Winssinger, N. (2008) Expanding the scope and orthogonality of PNA synthesis Eur. J. Org. Chem.: 3141-3148) followed by chloroacetylation and coupling with thioglycoside II and III affords products 7 and 8 with the same carbohydrate unit separate by a maximum distance of 15 Å and 19 Å respectively. For a greater distance between the carbohydrate units, the Fmoc group can be selectively removed and a 10 Å PEG spacer added prior to the chloroacetylations to obtain 10 after glycoside conjugation and release from the resin. Finally, to obtain different carbohydrate units on each side of the lysine residue, a first chloroacetylation/carbohydrate coupling is performed after the Fmoc deprotection but prior to Mtt removal. A second chloroacetylation/carbohydrate coupling can then be performed upon Mtt deprotection to obtain heterodimeric conjugates such as 11. Similar sequences were utilized to conjugate carbohydrate at the C-terminus of PNA starting from resin 12 to afford conjugates 13-17 bearing a single unit of α-1,2-mannose dimers or two units with distances ranging from 11.5 Å to 25 Å. The PNA-carbohydrate conjugate were then assembled into dimers and oligomers by hybridization to the appropriate DNA template. Considering the high persistent length of the double helix and the fact that all PNA sequences are 10 mers it can be anticipated that architecture such as entry 2, 3 and 15 (see FIG. 5) will be separated by 30 Å, 60 Å and 90 Å respectively. However, the fact that a PEG was included between the PNA and the carbohydrate allows for some level of flexibility.

A pilot library of over 30 assemblies was tested for their affinity to 2G12 by surface plasmon resonance (SPR). The antibody was immobilized accordingly to a previously described protocol. Under these conditions, no notable binding was observed for nonasaccharide 1, as previously reported by Danishefsky and coworkers (Krauss, I. J., Joyce, J. G., Finnefrock, A. C., Song, H. C., Dudkin, V. Y., Geng, X., Warren, J. D., Chastain, M., Shiver, J. W. & Danishefsky, S. J. (2007) Fully synthetic carbohydrate HIV antigens designed on the logic of the 2G12 antibody J Am Chem Soc 129: 11042-4; Dudkin, V. Y., Orlova, M., Geng, X., Mandal, M., Olson, W. C. & Danishefsky, S. J. (2004) Toward fully synthetic carbohydrate-based HIV antigen design: on the critical role of bivalency J Am Chem Soc 126: 9560-2) and in agreement with the binding mode reported by Wilson which involves four units of mannose disaccharide from multiple units of 1. Significant binding (μM) was observed for assemblies having the key α-1,2-mannose disaccharide units. However, the distance between the two units of this disaccharide was critical for the binding attesting to the importance of their cooperativity for avidity. Only assemblies bearing an 11 atom spacer between the two disaccharide units (structure 7 and 15) displayed any binding (entries 12-18, see FIG. 5). It is interesting to note that the distance between the two mannose units involved in the binding of nonasaccharide 1 is also 11 atoms. While the distance between the anomeric substituents is 10 Å through space (measured from PDB 1OP5), clearly, the shorter spacer present in structure 6 and 14 do not adequately replicate this geometry (entries 9-11) whereas longer spacer of structures 8, 10, 16, 17 (entry 22-25, 30-32) do not provide the adequate level of cooperativity. Following the same argument, assemblies based on the mannose trisaccharide fail to provide significant binding (entries 26-28). The topology of the supramolecular architecture also has a significant impact on binding. While the PEG spacer between the carbohydrate moiety and the PNA does provide a certain level of flexibility, a clear trend emerges by comparison of entries 12 to 15 with the shortest distance (entry 12) being best. Considering that a ca. 30 Å distance is required for cooperative binding to 2G12, the architecture used in entry 12 (the maximum distance between the branch points joining the carbohydrate units is 38.5 Å) would be most suitable whereas the architecture of entry 15 shows lower level of cooperative binding. The architecture in entry 16 has complimentary "sticky ends" and is anticipated to polymerize extensively. The value of 6.39 μM reported in FIG. 5 is for the DNA template and thus underestimates the affinity of the oligomeric polymer.

These results clearly demonstrate that it is possible to achieve cooperative binding between PNA-encoded fragments hybridized on a DNA-stand. The gp120 epitope has stimulated tremendous efforts towards the production of vaccines (Krauss, I. J., Joyce, J. G., Finnefrock, A. C., Song, H. C., Dudkin, V. Y., Geng, X., Warren, J. D., Chastain, M., Shiver, J. W. & Danishefsky, S. J. (2007) Fully synthetic carbohydrate HIV antigens designed on the logic of the 2G12 antibody J Am Chem Soc 129: 11042-4; Wang, S. K., Liang, P. H., Astronomo, R. D., Hsu, T. L., Hsieh, S. L., Burton, D. R. & Wong, C. H. (2008) Targeting the carbohydrates on HIV-1: Interaction of oligomannose dendrons with human monoclonal antibody 2G12 and DC-SIGN Proc. Natl. Acad. Sci. USA 105: 3690-5; Geng, X., Dudkin, V. Y., Mandal, M. & Danishefsky, S. J. (2004) In pursuit of carbohydrate-based HIV vaccines, part 2: The total synthesis of high-mannose-type gp120 fragments—evaluation of strategies directed to maximal convergence Angew. Chem. Int. Ed. Engl. 43: 2562-5; Warren, J. D., Geng, X. & Danishefsky, S. J. (2007) Synthetic glycopeptide-based vaccines Top. Curr. Chem. 267: 109-141). While this example illustrate the importance of multimeric recognition with controlled topology, the generality of this concept extends far beyond pathogen recognition (Imberty, A., Chabre, Y. M. & Roy, R. (2008) Glycomimetics and glycodendrimers as high affinity microbial anti-adhesins Chemistry 14: 7490-9) and is a recurrent feature in cellular recognition and communication as many signal transduction pathways are also regulated by multimeric interactions (Kiessling, L. L., Gestwicki, J. E. & Strong, L. E. (2006) Synthetic multivalent ligands as probes of signal transduction Angew. Chem. Int. Ed. Engl. 45: 2348-68).

EXAMPLE 11

Synthesis of a PNA-Encoded Library of Resorcyclic Acid Lactones

Figure 3:
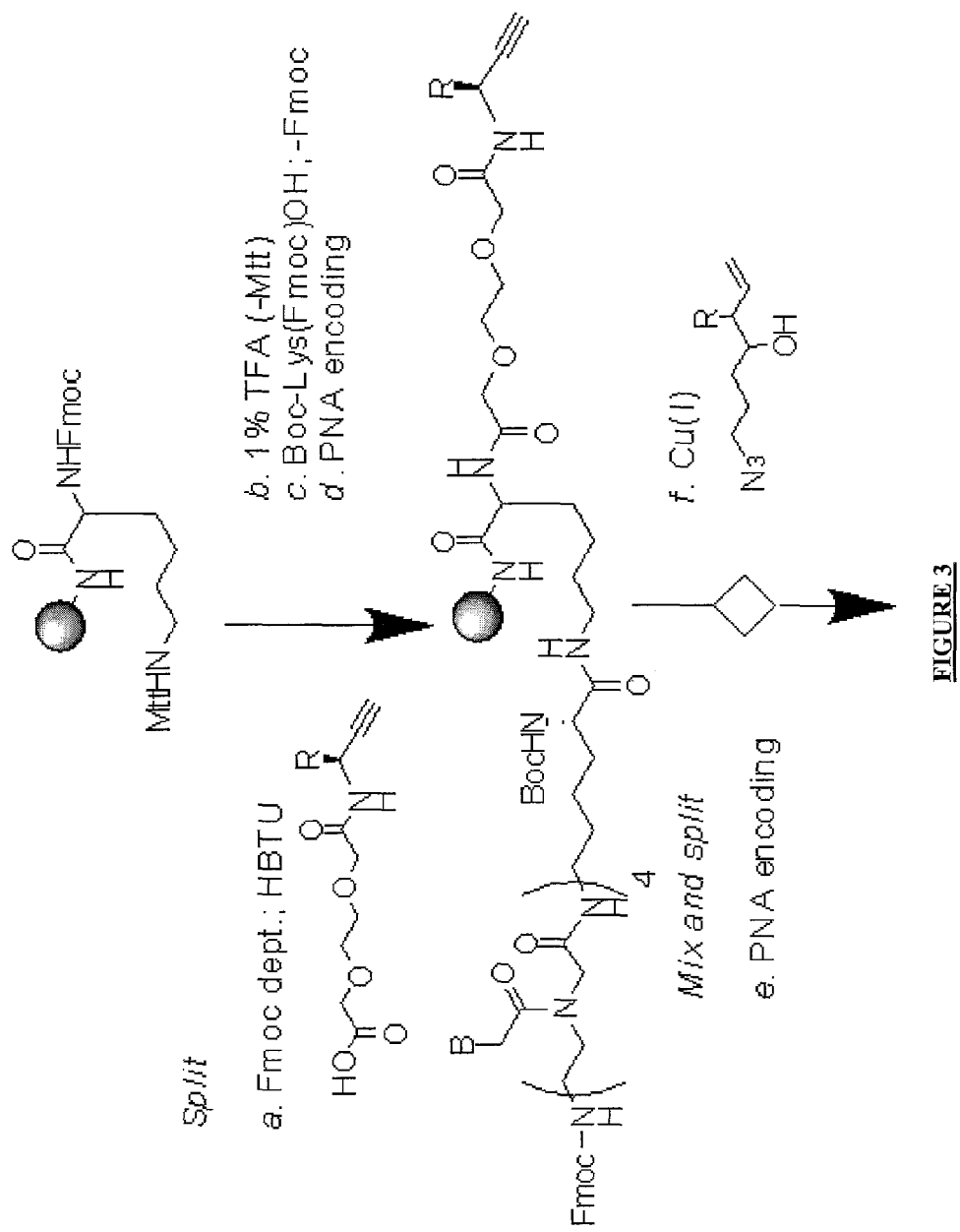
FIG. 3 shows the synthesis of a PNA-encoded library of resorcyclic acid lactones according to example 11.
Figure 3:
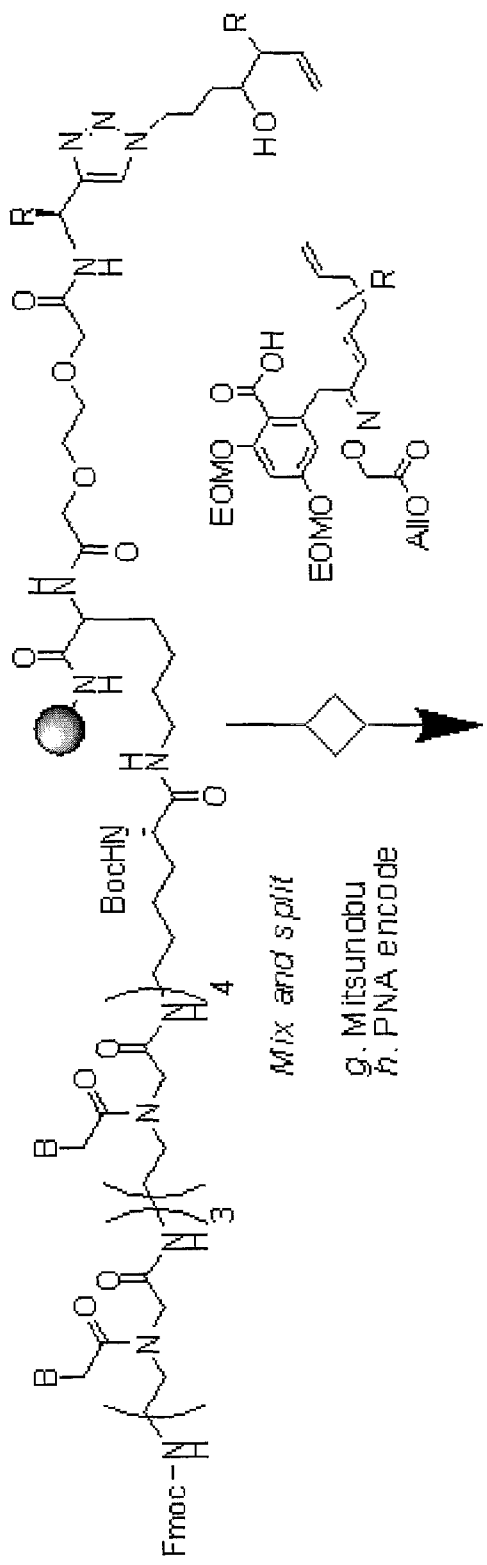
Figure 3:
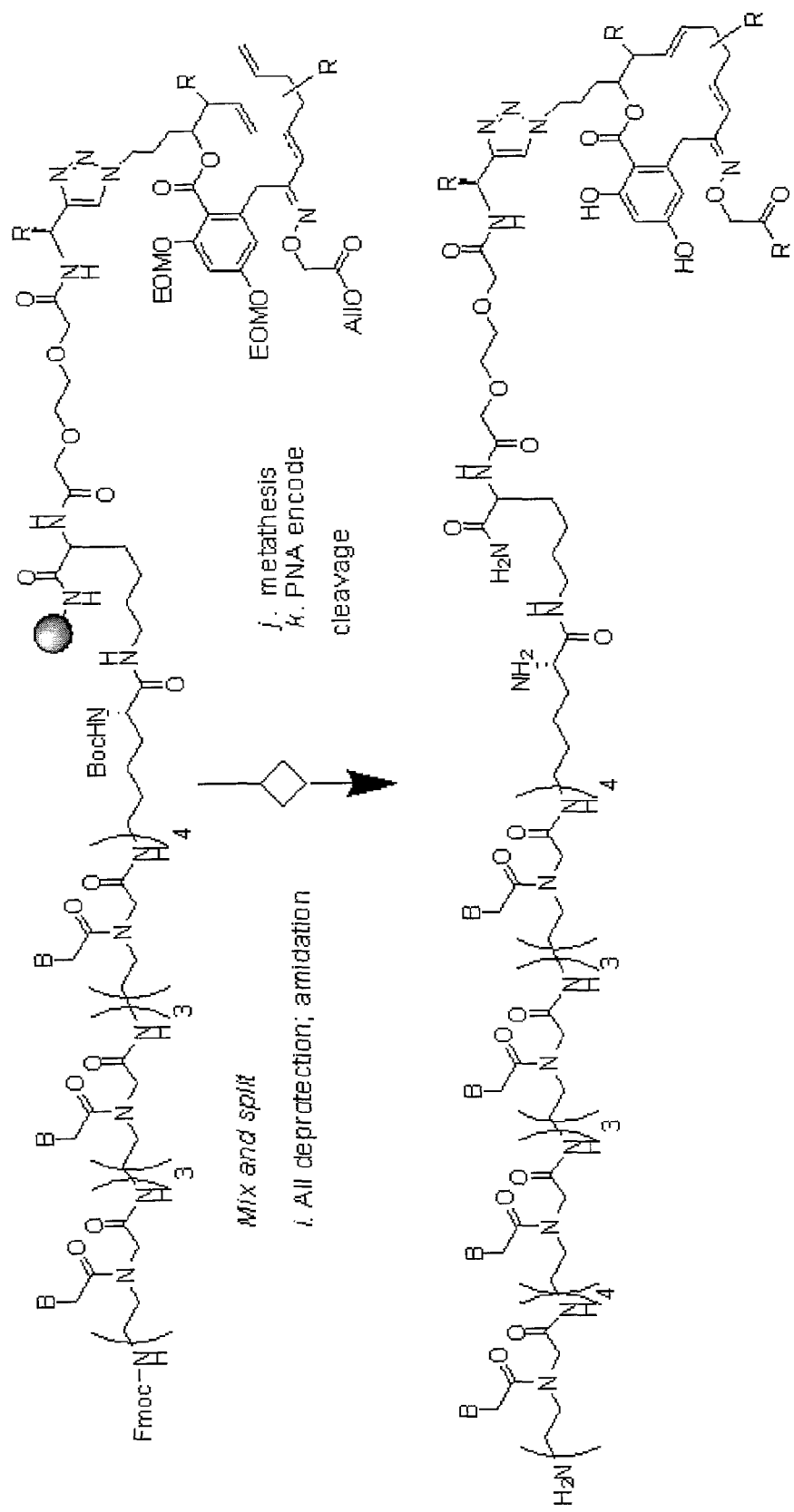
Figure 4:
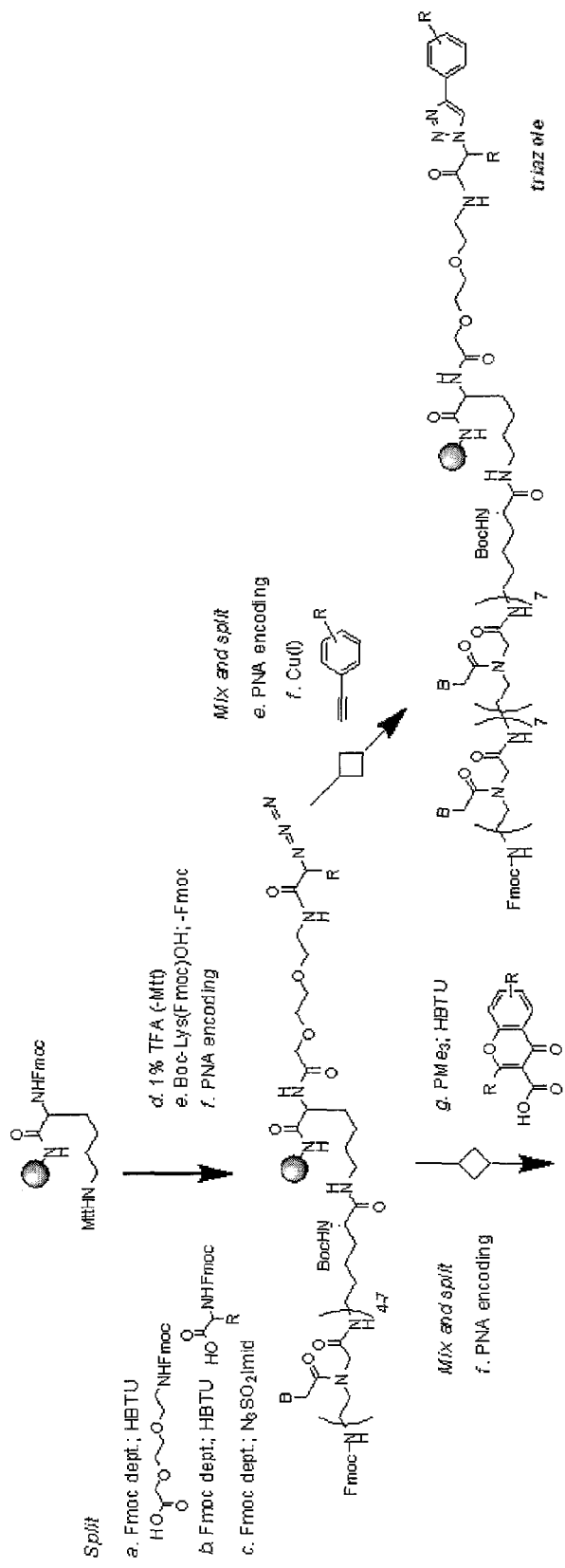
FIG. 4 represents the PNA-encoded split and mix synthesis of heterocyclic libraries by split and mix as described in examples 3 and 4.
Figure 4:
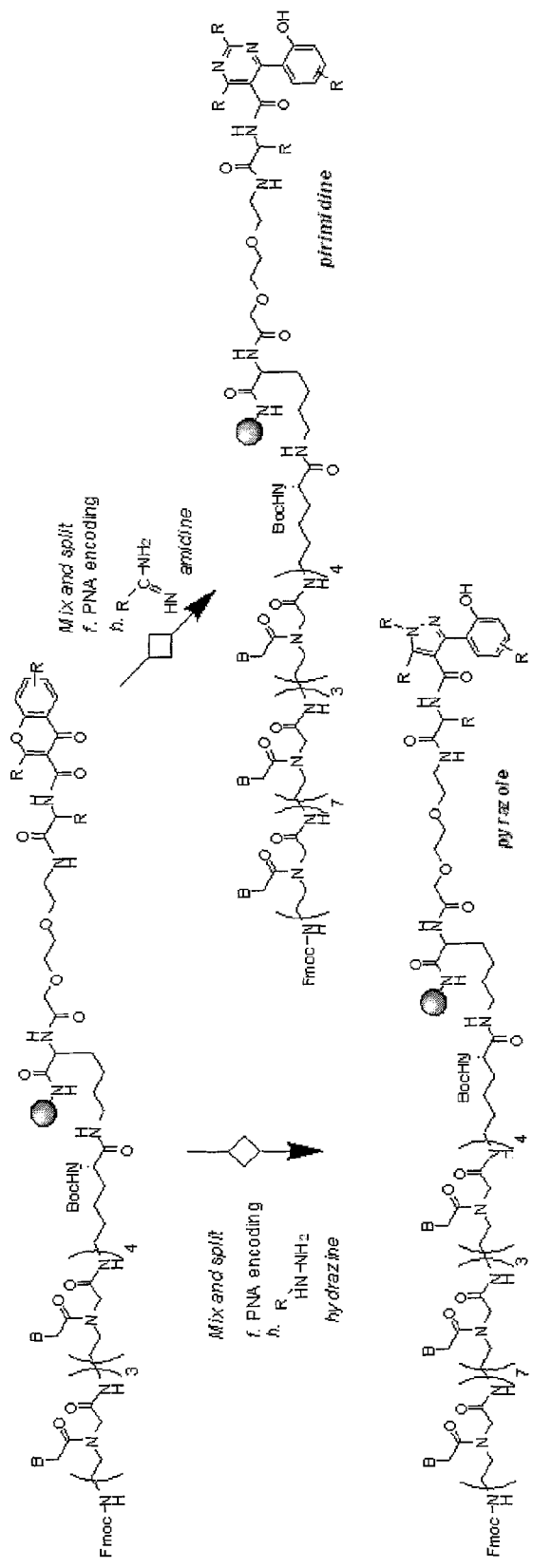

Said synthesis is illustrated in FIG. 3. Conditions are similar to those of example 3 and interpretable by a person skilled in the art.

The invention claimed is:

1. A method of preparing an adduct as potential drug candidate or catalyst having a biological or catalytic activity for a target of interest, comprising:
   a) providing at least one library of PNA-encoded molecules and a library of nucleotide chains,
   b) hybridizing said at least one library of PNA-encoded molecules onto said library of nucleotide chains,
   c) bringing into contact the resulting library of PNA-encoded molecule(s)/nucleotide chain hybrid(s) with said target of interest,
   d) selecting the fittest PNA-encoded molecule(s)/nucleotide chain hybrid(s) for the target of interest,
   e) amplifying nucleotide chain(s) obtained from the previously mentioned fittest PNA-encoded molecule(s)/nucleotide chain hybrid(s),
   f) optionally bringing into contact said amplified nucleotide chain(s) with one or more library of PNA-encoded molecules, the library of PNA-encoded molecules having a content identical to that of said library(s) of PNA-encoded molecules provided in step a), or containing some modification, then hybridizing said amplified nucleotide chains(s) and said library of PNA-encoded molecules and repeating steps c) to e), step f) being repeated until a convergence towards one or several consensus sequences is obtained,
   g) identifying said nucleotide chain(s) obtained in step e) or f), each of said nucleotide chain(s) corresponding to at least one PNA-encoded molecule of the at least one library of PNA-encoded molecules recited in step a),
   h) determining at least one consensus structure provided by the nucleotide chain(s) identified in step g), said at least one consensus structure having a high-affinity to said target of interest,
   i) synthesizing a covalent adduct mimicking the consensus structure identified in step h), and
   j) validating the biological or catalytic activity of the covalent adduct.

2. The method according to claim 1, wherein step f) is repeated less than 20 times.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:

```
<223> OTHER INFORMATION: 5'-primer (20mer)

<400> SEQUENCE: 1
acgagaggct cacaacaggc                                          20

<210> SEQ ID NO 2
<211> LENGTH: 20
<212> TYPE: DNA
<213> ORGANISM: Artificial Sequence
<220> FEATURE:
<223> OTHER INFORMATION: 3'-anti-primer (20mer)

<400> SEQUENCE: 2
ggatagacaa taacgacgac                                          20

<210> SEQ ID NO 3
<211> LENGTH: 20
<212> TYPE: DNA
<213> ORGANISM: Artificial Sequence
<220> FEATURE:
<223> OTHER INFORMATION: 5-primer (20mer)
<220> FEATURE:
<221> NAME/KEY: misc_feature
<222> LOCATION: (1)..(1)
<223> OTHER INFORMATION: Modified at N-terminus by biotin group

<400> SEQUENCE: 3
gcctgttgtg agcctctcgt                                          20

<210> SEQ ID NO 4
<211> LENGTH: 20
<212> TYPE: DNA
<213> ORGANISM: Artificial Sequence
<220> FEATURE:
<223> OTHER INFORMATION: 3'-anti-primer (20mer)
<220> FEATURE:
<221> NAME/KEY: misc_feature
<222> LOCATION: (1)..(1)
<223> OTHER INFORMATION: Modified at N-terminus by cyanine-3 group (Cy3)

<400> SEQUENCE: 4
ggatagacaa taacgacgac                                          20
```